United States Patent
Medendorp, Jr. et al.

(10) Patent No.: US 12,201,757 B2
(45) Date of Patent: Jan. 21, 2025

(54) PHOTOACTIVATED BLOOD PRODUCTS AND METHODS AND APPARATUS FOR FABRICATION AND USE OF SAME

(71) Applicant: KNOW Bio, LLC, Durham, NC (US)

(72) Inventors: Nicholas William Medendorp, Jr., Durham, NC (US); Katelyn Reighard Crizer, Durham, NC (US)

(73) Assignee: KNOW Bio, LLC, Morrisville, NC (US)

( * ) Notice: Subject to any disclaimer, the term of this patent is extended or adjusted under 35 U.S.C. 154(b) by 504 days.

(21) Appl. No.: 17/611,782

(22) PCT Filed: May 22, 2020

(86) PCT No.: PCT/US2020/034287
§ 371 (c)(1),
(2) Date: Nov. 16, 2021

(87) PCT Pub. No.: WO2020/242971
PCT Pub. Date: Dec. 3, 2020

(65) Prior Publication Data
US 2022/0233752 A1    Jul. 28, 2022

Related U.S. Application Data

(60) Provisional application No. 62/852,732, filed on May 24, 2019.

(51) Int. Cl.
*A61N 5/06*        (2006.01)
*A61K 35/16*       (2015.01)
(Continued)

(52) U.S. Cl.
CPC .......... *A61M 1/0259* (2013.01); *A61K 35/16* (2013.01); *A61K 38/1858* (2013.01); *A61M 2202/0415* (2013.01); *A61M 2202/0445* (2013.01)

(58) Field of Classification Search
CPC .................................................... A61N 5/062
See application file for complete search history.

(56) References Cited

U.S. PATENT DOCUMENTS 8,240,312 B2    8/2012  Feuerstein et al.
8,435,273 B2    5/2013  Lum et al.
(Continued)

FOREIGN PATENT DOCUMENTS

CN    102573943 A        7/2012
CN    105039303 A   *   11/2015
(Continued)

OTHER PUBLICATIONS

English machine translation of Wu et al., CN 105039303 A, 2015.*
(Continued)

*Primary Examiner* — Rosanne Kosson
(74) *Attorney, Agent, or Firm* — Withrow & Terranova, P.L.L.C.

(57) ABSTRACT

Embodiments provide methods and apparatus for fabricating blood products, such as platelet-rich plasma, containing elevated concentrations of growth factors such as platelet derived growth factor. The platelet-rich plasma can be autologous, and the concentration of growth factors (e.g., platelet derived growth factor) is elevated relative to other samples isolated from the same subject. The platelet-rich plasma can be used to promote tissue regeneration, including wound healing, joint repair, hair growth, and the like. The compositions can be combined with stem cells and used to treat disorders otherwise treated with stem cells. The growth factors present in the samples can direct the differentiation of the stem cells.

16 Claims, 8 Drawing Sheets

(51) Int. Cl.
*A61K 38/18* (2006.01)
*A61M 1/02* (2006.01)

(56) References Cited

U.S. PATENT DOCUMENTS

| | | | |
|---|---|---|---|
| 8,838,228 | B2 | 9/2014 | Beisang, III et al. |
| 9,901,747 | B2 | 2/2018 | Gamelin et al. |
| 10,525,275 | B2 | 1/2020 | Stasko et al. |
| 10,639,498 | B2 | 5/2020 | Enwemeka et al. |
| 10,780,189 | B2 | 9/2020 | Randers-Pehrson et al. |
| 10,981,017 | B2 | 4/2021 | Enwemeka et al. |
| 11,266,855 | B2 | 3/2022 | Enwemeka et al. |
| 11,318,325 | B2 | 5/2022 | Rezaie et al. |
| 2007/0262020 | A1 | 11/2007 | Wang |
| 2017/0231901 | A1* | 8/2017 | Meng .................. A61Q 19/08 424/93.7 |
| 2021/0052760 | A1 | 2/2021 | Bouschbacher et al. |
| 2021/0196977 | A1 | 7/2021 | Zhang |
| 2021/0346500 | A1 | 11/2021 | Schikora |
| 2021/0402212 | A1 | 12/2021 | Schupp et al. |
| 2022/0088409 | A1 | 3/2022 | Dombrowksi et al. |

FOREIGN PATENT DOCUMENTS

| | | |
|---|---|---|
| WO | 9211057 A1 | 7/1992 |
| WO | 9606647 A1 | 3/1996 |
| WO | 2017011612 A1 | 1/2017 |

OTHER PUBLICATIONS

Second Office Action for Chinese Patent Application No. 2020800384255, mailed Jun. 14, 2023, 13 pages.
Cavallo, et al., "Platelet-Rich Plasma: The Choice of Activation Method Affects the Release of Bioactive Molecules," Biomed Research International, vol. 2016, Article ID 6591717, 8 pages.
Dhurat, et al., "Principles and Methods of Preparation of Platelet-Rich Plasma: A Review and Author's Perspective," Journal of Cutaneous and Aesthetic Surgery, Oct. 2014, vol. 7, Issue 4, pp. 189-197.
Erlandsson, et al., "Immature Neurons From CNS Stem Cells Proliferate in Response to Platelet-Derived Growth Factor," The Journal of Neuroscience, vol. 21, Issue 10, May 2001, pp. 3483-3491.
Lana, et al., "Contributions for classification of platelet rich plasma—proposal of a new classification: MARSPILL," Regenerative Medicine, vol. 12, Issue 5, Jul. 2017, pp. 565-574.
Lubart, et al., "A Possible Mechanism for the Bactericidal Effect of Visible Light," Laser Therapy, vol. 20, Issue 1, 2011, JMLL, pp. 17-22.
Saura, et al., "An Antiviral Mechanism of Nitric Oxide: Inhibition of a Viral Protease," Immunity, vol. 10, Issue 1, Jan. 1999, Cell Press, pp. 21-28.
Takahashi, et al., "Induction of Pluripotent Stem Cells from Adult Human Fibroblasts by Defined Factors," Cell, vol. 131, Issue 5, Nov. 2007, Elsevier Inc., pp. 861-872.
Zhevago, et al., "Pro- and Anti-inflammatory Cytokine Content in Human Peripheral Blood after Its Transcutaneous (in Vivo) and Direct (in Vitro) Irradiation with Polychromatic Visible and Infrared Light," Photomedicine and Laser Surgery, vol. 24, Issue 2, 2006, Mary Ann Liebert, Inc., pp. 129-139.
International Search Report and Written Opinion for International Patent Application No. PCT/US2020/034287, mailed Sep. 28, 2020, 9 pages.
Alzyoud, et al., "Effect of light-emitting diodes, platelet-rich plasma, and their combination on the activity of sheep tenocytes," Lasers in Medical Science, vol. 34, Issue 4, Oct. 13, 2018, Springer, pp. 759-766.
Paterson, et al., "Intra-articular injection of photo-activated platelet-rich plasma in patients with knee osteoarthritis: a double-blind, randomized controlled pilot study," BMC Musculoskeletal Disorders, vol. 17, Dec. 2016, 9 pages.
First Office Action for Chinese Patent Application No. 2020800384255, mailed Dec. 2, 2022, 13 pages.
Extended European Search Report for European Patent Application No. 20814639.9, mailed Jan. 2, 2023, 8 pages.
Decision of Rejection for Chinese Patent Application No. 2020800384255, mailed Oct. 24, 2023, 9 pages.

* cited by examiner

PHOTOACTIVATED BLOOD PRODUCTS AND METHODS AND APPARATUS FOR FABRICATION AND USE OF SAME

This application is a 35 U.S.C. § 371 national phase filing of International Application No. PCT/US2020/034287, filed May 22, 2020, which claims the benefit of U.S. provisional patent application Ser. No. 62/852,732, filed May 24, 2019, the disclosures of which are incorporated herein by reference in their entirety.

BACKGROUND

The inventive subject matter relates to blood plasma products and methods and apparatus for fabrication and use of the same.

Autologous platelet-rich plasma (aPRP) is used for a variety of therapeutic purposes. The concentration of certain therapeutic components of PRP, such as growth factors, are known to influence outcomes across many therapeutic uses, for example tissue regrowth. PRP is a non-surgical treatment, administered by injection. It differs from stem cells in that it uses the healing factors found in blood plasma to heal degenerative or acute damage in joints.

For a given patient, enhancement of growth factors within their autologous blood product can result in enhanced tissue growth. Accordingly, there is a need for methods to increase the concentration of growth factors (e.g., platelet derived growth factor) in compositions of blood and blood products such as platelet-rich plasma.

Stem cell therapy is also typically a non-surgical treatment, administered by injection, that uses a patient's own stem cells to accelerate healing. Stem cells are undifferentiated cells, which, when they differentiate, become other types of cells. There are four main types of stem cells, namely, cord blood/amniotic fluid stem cells, embryonic stem cells, non-embryonic (adult) stem cells, and induced pluripotent stem cells (iPSCs).

Cord blood/amniotic fluid stem cells are obtained before or at the time of birth, and frozen for later use. This type of stem cell is only available for individuals whose parents had the forethought to store these cells, so for older patients looking for stem cell therapy, it is unlikely that these cells are available.

Embryonic stem cells are "creator" cells that can be coaxed to develop into almost type of tissue. In some cases, this can be beneficial, but in others, this is harmful, as the cells can develop into tumors instead of a desired type of tissue. Further, as these are not autologous stem cells, they can be rejected. In contrast, adult stem cells are "repair" cells with a limited range of transformation. Also, since these cells are typically derived from the patient's own body, i.e., are autologous stem cells, there is no risk of rejection.

Adult stem cells can be obtained from a variety of sources, though the main sources are bone marrow-derived stem cells and adipose-derived stem cells, though stem cells are also found in a patient's peripheral blood.

Induced pluripotent stem cells (iPSCs) are adult cells that have been genetically re-programmed to an embryonic stem cell-like state by being forced to express genes and factors important for maintaining the defining properties of embryonic stem cells.

The iPSC technology was pioneered by Shinya Yamanaka's lab in Kyoto, Japan, who showed in 2006 that the introduction of four specific genes (named Myc, Oct3/4, Sox2 and Klf4) encoding transcription factors could convert somatic cells into pluripotent stem cells. Yamanaka's group successfully transformed human fibroblasts into iPSCs with the same four pivotal genes, Oct4, Sox2, Klf4, and cMyc, using a retroviral system (Takahashi et al., Cell. 131 (5): 861-72 (2007)). In addition to fibroblasts, iPSCs can also be produced from human keratinocytes and peripheral blood cells.

Since iPSCs can be derived directly from adult tissues, they not only bypass the need for embryos, but can be made in a patient-matched manner, which means that each individual could have their own pluripotent stem cell line, without the risk of immune rejection.

It is believed that once stem cells are administered, cytokines at sites of injury attract the stem cells to where they are needed. Once there, various growth factors can affect how the stem cells differentiate.

Stem cells injected into an area by themselves may remain relatively quiescent. The stem cells tend not to function well without PRP or some component of it also being present. The PRP contributes growth factors and stimulating proteins, which directly affect stem cells. Signaling factors instruct the body to send stem cells to the area of damage and at the same time cause the stem cells to reproduce and begin repair.

Outside of the United States, a treating physician might extract bone marrow, typically from the pelvis or hip, and/or extract adipose tissue (fat), and isolate stem cells from the extracted samples. The stem cells might then be activated and multiplied using one or more growth factors. In this activation process, stem cells can be customized for the purpose for which they will be used in treatment. For example, they can be activated to build muscle tissue for the heart, to rebuild blood vessels in the extremities or lungs or into neural cells for the central nervous system.

In the U.S., current law does not permit the treating physician to mix stem cells with exogenous growth factors. So, the treatment relies on endogenous growth factors to cause the stem cells to differentiate into a desired tissue type.

Since endogenous growth factors (as opposed to exogenous growth factors) are present in a patient's own plasma-rich protein (PRP), a variety of different treatments have been developed where stem cells, including adipose and/or bone marrow-derived stem cells, are administered along with plasma-rich protein (PRP). Growth factors in the PRP can direct stem cell differentiation. Stem cells (peripheral blood stem cells) are also present in the PRP, which stem cells can be combined with stem cells derived from adipose tissue and/or bone marrow. In some cases, human growth hormone (HGH) is administered along with the PRP and stem cells.

One limitation of using PRP is that the amount of growth factors is limited. Growth factors can aid in wound healing on their own and can aid in the differentiation of stem cells to other types of cells, which cells aid in wound healing. It would be advantageous to provide ways to increase the amount of endogenous growth factors in PRP, particularly when combined with stem cell therapy.

SUMMARY

According to some embodiments, methods include processing a quantity of blood by controlling a spectral content of light applied to the quantity of blood such that a concentration of a growth factor in the quantity of blood is increased. A plasma product including the growth factor is extracted from the processed quantity of blood.

In some embodiments, controlling the spectral content of the applied light may include providing light with enhanced power in a wavelength range from about 600 nm to about 1500 nm. In further embodiments, controlling the spectral content of the applied light may include providing light with enhanced power in a wavelength range from about 600 nm to about 900 nm and wherein the growth factor comprises a platelet-derived growth factor (PDGF). Providing light with enhanced power in wavelength range from about 600 nm to about 900 nm may include irradiating the quantity of blood using a light-emitting diode (LED) light source.

According to further aspects, the methods may further include controlling a radiant energy of the applied light. Controlling the radiant energy of the applied light may include controlling an exposure time of the applied light.

In some embodiments, controlling the spectral content of the applied light may include irradiating the quantity of blood with a solid-state light source. The solid-state light source may include a LED light source. The LED light source may have a maximum spectral power in a wavelength range from about 600 nm to about 1500 nm.

According to further embodiments, controlling the applied light may include irradiating a transparent vessel containing the quantity of blood with a spectrally-selective selective light source while the transparent vessel is housed in an enclosure that blocks exposure of the vessel to ambient light.

In some embodiment, methods may further include administering a therapeutically effective amount of a composition including the plasma product to tissue of a subject to promote tissue regeneration. A concentration of the growth factor in the composition may be at least about 50% higher than in an un-irradiated sample of platelet-rich plasma isolated from a source of the quantity of blood. The quantity of blood may be derived from the subject.

Still further embodiments provide an apparatus including an enclosure configured for installation of a blood-carrying vessel therein such that blood in the installed vessel is shielded from ambient light. The apparatus further includes a light source in the enclosure and configured to expose the blood in the installed vessel to light having its maximum spectral power in a wavelength range from about 600 nm to about 1500 nm. The light source may be configured to expose the blood in the installed vessel to light having its maximum spectral power in a range from about 600 nm to about 900 nm. The light source may include an LED light source.

In one embodiment, methods for increasing the concentration of one or more growth factors (e.g., platelet derived growth factor) in a biological sample, which can be an autologous sample, comprising irradiating the sample with light, are disclosed.

In another embodiment, methods are disclosed for increasing the concentration of growth factors in compositions of blood and/or blood products, including but not limited to autologous compositions, by irradiating the blood and/or blood products with light.

In some aspects of these embodiments, the compositions comprise blood samples derived from a subject (i.e., autologous samples). In other aspects of this embodiment, the compositions comprise whole blood or fractions of whole blood (e.g., platelet-rich plasma, including autologous platelet-rich plasma).

In another embodiment, methods for increasing the concentration of a growth factor in a sample of platelet-rich plasma are disclosed. The methods involve irradiating a sample of whole blood with light and isolating the sample of platelet-rich plasma from the sample of irradiated whole blood.

In still another embodiment, compositions comprising irradiated blood, blood products, or PRP that include enhanced concentrations of one or more growth factors are also disclosed. In one aspect of this embodiment, the compositions comprise an irradiated autologous platelet-rich plasma (PRP), wherein the concentration of an autologous growth factor in the composition is at least about 30 percent, preferably at least 40%, and still more preferably, at least 50% higher than in an un-irradiated sample of platelet-rich plasma isolated from the same autologous source.

In some embodiments, the concentration of autologous growth factor is at least about 100%, at least 150, at least about 200%, at least about 250%, at least about 300%, at least about 350%, at least about 400%, at least about 450%, or at least about 500% higher than in an un-irradiated sample of platelet-rich plasma isolated from the same autologous source.

In some embodiments, the composition does not comprise exogenous growth factor. In some embodiments, the growth factor is platelet-derived growth factor. In other embodiments, the composition further comprises one or more exogenous growth factors. In still other embodiments, the composition further comprises human growth hormone (HGH), analogs of HGH, and/or compounds which promote the release of HGH.

In some embodiments, the compositions are combined with stem cells. In embodiments, the stem cells are autologous stem cells, and in other embodiments, the stem cells are embryonic stem cells. Representative autologous stem cells include adipose tissue-derived stem cells, peripheral blood-derived stem cells, and bone marrow-derived stem cells. Mesenchymal stem cells (MSCs) are multipotent stromal cells that can differentiate into a variety of cell types, including osteoblasts (bone cells), chondrocytes (cartilage cells), myocytes (muscle cells) and adipocytes (fat cells which give rise to marrow adipose tissue). In some aspects of these embodiments, human growth hormone, analogs thereof, and/or compounds which promote the production and/or release of human growth hormone are also present.

These compositions can be used to treat subjects otherwise treatable with stem cells, where the increased concentration of one or more growth factors assists in the differentiation of the stem cells into desired tissue types, and/or provides other healthful benefits.

Methods for treating a patient with these compositions are also disclosed. The compositions can be administered to promote tissue growth, to repair joints, and the like. In some embodiments, the composition is PRP, which, in some respects, is isolated from an autologous sample of whole blood.

The methods of treatment include promoting tissue regeneration, including wound healing, in a subject in need thereof. These methods involve administering a therapeutically effective amount of a composition comprising irradiated autologous platelet-rich plasma to the tissue of the subject. The concentration of one or more autologous growth factors, which in one embodiment is or comprises platelet-derived growth factor (PDGF), in the composition is at least about 50% higher than in an un-irradiated sample of platelet-rich plasma isolated from the same autologous source.

In one aspect of these embodiments, the concentration of an autologous growth factor in the composition, such as PDGF, is at least about 50% higher than in an un-irradiated sample of platelet-rich plasma isolated from the same autologous source. In one aspect of these embodiments, the composition is or comprises platelet-rich plasma, which can be, but need not be, isolated from an autologous sample of whole blood.

In some embodiments, compositions comprising platelet-rich plasma are injected into the tissue of the subject or injected directly into one or more joints. In other embodiment, compositions are topically applied to the tissue.

In some embodiments, the tissue regeneration comprises increasing hair growth, reducing skin wrinkles, reducing fine lines in the skin, increasing skin elasticity, or treating burns.

Hair growth can be promoted, for example, by administering a therapeutically effective amount of a composition comprising irradiated autologous platelet-rich plasma to the skin of the subject, such as the scalp of a subject. In some embodiments, the skin of the subject comprises a plurality of hair follicles. The composition can be applied topically or injected into the skin, such as the scalp.

Skin wrinkles and fine lines in the skin can be reduced, and skin elasticity can be increased, for example, by topically applying the compositions to, or injecting the compositions into, the skin.

Burns can be treated by topically applying the compositions to the burned skin.

In other embodiments, the subject in need thereof has a tendon injury, tendinopathy, lateral epicondylitis, patellar tendinopathy, plantar fasciitis, rotator cuff tendinopathy, Achilles tendinopathy, undergone rotator cuff repair, undergone Achilles tendon repair, joint injury from arthritis, osteoarthritis, ankle sprain, bone fracture, bone fracture with nonunion, muscle injury, and/or muscle strain. In some aspects of these embodiments, the osteoarthritis is of the knee, shoulder, elbow, hip, back, hands, and/or feet. Methods for treating these subjects involve orthopedic tissue regeneration, including regenerating tendons, muscles, cartilage, ligament and/or bone, using the compositions described herein. The compositions can be injected into a damaged joint, or at or near where a bone has been fracture, or a muscle, ligament or tendon has been injured.

In one embodiment, the methods for increasing the concentration of a growth factor in the samples, such as blood or blood products, including platelet-rich plasma, whether or not the samples are autologous, involve irradiating the sample with light with a wavelength of at least about 600 nanometers (e.g., about 600 nanometers to about 1500 nanometers). In some embodiments, the light has a wavelength of at least about 650 nanometers, at least about 700 nanometers, at least about 750 nanometers, at least about 800 nanometers, at least about 850 nanometers, at least about 900 nanometers, at least about 950 nanometers, at least about 1000 nanometers, or between about 1000 to about 1500 nanometers. In some embodiments, the light does not comprise ultraviolet light.

In some embodiments, combinations of wavelengths are used. In some aspects of these embodiments, each wavelength promotes the production of a different growth factor. In some embodiments, the growth factor is platelet-derived growth factor.

In some embodiments, the radiant exposure of the whole blood to light is at least about 1 $J/cm^2$, at least about 2 $J/cm^2$, at least about 3 $J/cm^2$, at least about 4 $J/cm^2$, at least about 5 $J/cm^2$, at least about 6 $J/cm^2$, at least about 7 $J/cm^2$, at least about 8 $J/cm^2$, at least about 9 $J/cm^2$, at least about 10 $J/cm^2$, at least about 11 $J/cm^2$, at least about 12 $J/cm^2$, at least about 13 $J/cm^2$, at least about 14 $J/cm^2$, at least about 15 $J/cm^2$, at least about 20 $J/cm^2$, at least about 25 $J/cm^2$, at least about 30 $J/cm^2$, at least about 35 $J/cm^2$, at least about 40 $J/cm^2$, at least about 45 $J/cm^2$, or at least about 50 $J/cm^2$.

In some embodiments, the whole blood is irradiated with light for at least about 1 second, at least about 2 seconds, at least about 3 seconds, at least about 4 seconds, at least about 5 seconds, at least about 6 seconds, at least about 7 seconds, at least about 8 seconds, at least about 9 seconds, at least about 10 seconds, at least about 20 seconds, at least about 30 seconds, at least about 40 seconds, at least about 50 seconds, at least about 60 seconds, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 20 minutes, at least about 30 minutes, at least about 40 minutes, at least about 50 minutes, or at least about 60 minutes.

In some embodiments, the light has a wavelength of at least about 600 nanometers and the radiant exposure of the whole blood to light is at least about 5 $J/cm^2$. In some embodiments, the whole blood is irradiated for at least about 1 minute.

In some embodiments, the light has a wavelength of at least about 700 nanometers and the radiant exposure of the whole blood to light is at least about 7 $J/cm^2$. In some embodiments, the whole blood is irradiated for at least about 5 minutes.

In some embodiments, the light has a wavelength of at least about 800 nanometers and the radiant exposure of the whole blood to light is at least about 9 $J/cm^2$. In some embodiments, the whole blood is irradiated for at least about 7 minutes.

In some embodiments, the light has a wavelength of at least about 850 nanometers and the radiant exposure of the whole blood to light is at least about 10 $J/cm^2$. In some embodiments, the whole blood is irradiated for at least about 10 minutes.

In some embodiments, the light is non-coherent light, which includes LED and OLED light. In other embodiments, the light is laser light. In still other embodiments, combinations of light sources are used.

In some embodiments, a sample of whole blood is agitated during exposure. In some embodiments, the agitation comprises mechanical stirring. In some embodiments, the agitation comprises flowing the whole blood through an irradiation chamber. In some embodiments, the agitation comprises pumping the whole blood through an irradiation chamber. In some embodiments, the agitation comprises moving a vessel (e.g., an optically transparent vessel) containing the whole blood. In some embodiments, the agitation comprises inverting a vessel containing the whole blood. In some embodiments, the agitation comprises rolling a vessel containing the whole blood.

In some embodiments, isolating the sample of platelet-rich plasma from the sample of irradiated whole blood comprises: centrifuging the sample of irradiated whole blood to separate the components of the whole blood; removing a portion of platelet-poor plasma; re-suspending the platelets in the remaining amount of platelet-poor plasma to give a sample of platelet-rich plasma; and separating the platelet-rich plasma from the remaining components of the whole blood. In some embodiments, the platelet-rich plasma is isolated from the sample of irradiated whole blood within about 10 minutes of irradiation.

Additional features and advantages of the present disclosure are set forth in the Detailed Description below.

DETAILED DESCRIPTION

Figure 1:
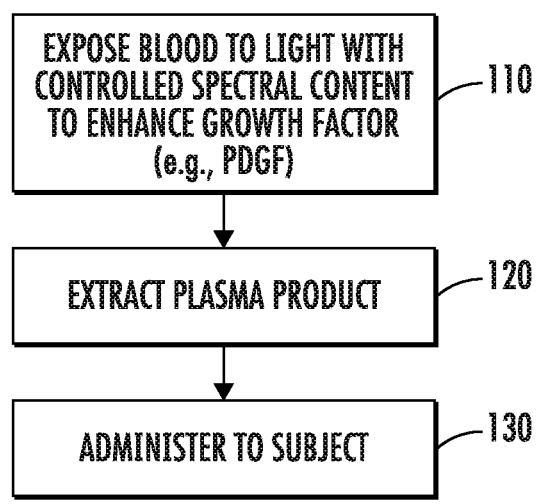
FIG. 1 is a diagram illustrating operations for fabricating a plasma product according to some embodiments.

Some embodiments provide methods of preparing samples of blood and/or blood products, such as platelet-rich plasma (PRP), containing elevated concentrations of certain growth factors, such as platelet derived growth factor. In some embodiments, the blood or blood product is an autologous composition isolated from a subject, and the concentration of growth factors (e.g., platelet derived growth factor) is elevated relative to other samples isolated from the same subject. The blood or blood products can be used to promote tissue growth, e.g., hair growth.

Some embodiments relate to methods of irradiating whole blood to increase the concentration of certain growth factors (such as platelet derived growth factor) in the whole blood and resulting blood products (e.g., platelet-rich plasma). As set forth herein, the wavelength and the radiant exposure of the whole blood to light can affect the relative increase of the growth factors in the whole blood and resulting blood products. The irradiated blood and resulting blood products can be administered back to the subject from whom the whole blood was initially taken (e.g., the whole blood and/or blood products can be autologous).

The whole blood and/or blood products can be used to treat disease and/or for cosmetic purposes. For example, autologous platelet-derived plasma that is enriched with platelet derived growth factor as taught herein can be used to promote tissue growth, e.g., to promote hair growth or re-growth.

The present disclosure teaches methods of increasing the concentration of growth factors such as platelet derived growth factor in compositions comprising blood or blood products isolated from subjects. As set forth herein, whole-blood isolated from a subject can be irradiated with light to increase the concentration of growth factors (e.g., platelet derived growth factor) compared with whole-blood isolated from the same subject that has not been irradiated. Accordingly, the present disclosure allows for the preparation of autologous samples of blood or blood products that can be enriched in autologous growth factors such as platelet derived growth factor.

One advantage of the compositions and methods described herein is that they enrich a patient's own (i.e., autologous) blood samples with the patient's own growth factors. This can reduce or eliminate the need to add exogenous growth factors, such as platelet derived growth factor, to the blood or blood products before administering those blood products to the subject (e.g., for a therapeutic purpose). The methods disclosed herein reduce the need to add other exogenous chemicals to the autologous blood or blood product to increase the concentration of growth factors in the blood or blood product.

Another advantage is that the amount of enrichment of growth factors (e.g., platelet derived growth factor) in the blood or blood products can be adjusted predictably based on the selection of light application parameters. For example, an autologous blood product can be prepared that can be more or less enriched for certain growth factors (e.g., platelet derived growth factor) based on the wavelength, duration, and/or intensity (e.g., radiant exposure) of the light.

Another advantage is that non-coherent light can be used to increase the concentration of growth factors in the blood or blood products. Accordingly, some embodiments include methods that do not require expensive equipment to increase the concentration of growth factors in blood or blood products.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the term "subject" encompasses mammals and non-mammals. Examples of mammals include, but are not limited to, any member of the class Mammalia: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment, the mammal is a human.

As used herein, the term "autologous" is understood to mean that a given sample or composition (e.g., a sample or composition of whole blood or blood product such as platelet-rich plasma) is obtained from a particular individual (e.g., an individual such as a human) and is administered to the same individual (i.e., back to the same individual). For example, isolating a sample of whole blood from an individual and later administering the same sample of whole blood back to the individual is an example of administering an autologous whole blood sample to the individual. Similarly, isolating a sample of plasma (e.g., platelet-rich plasma) from an individual and later administering the same sample of plasma (e.g., platelet-rich plasma) back to the individual is an example of administering an autologous plasma (e.g., platelet-rich plasma) sample to the individual.

As used herein, "orthopedic tissue regeneration" refers to regeneration associated with the correction, prevention, treatment or amelioration of deformities, disorders and injuries of the skeleton and associated tissues and structures, such as tendons, ligaments and muscles.

As used herein, "wound" refers to any damaged tissue, for example following trauma or surgery. Wounds in mammals, include, but are not limited to bed sores, ulcers, lacerations and burns, graft sites (graft donor and acceptor sites), fistulas, periodontal tissue damages, diabetic non-healing wounds, consequences of traumas or any surgery act. In some embodiments, the wound is a bed sore, ulcer, laceration, burns, graft site, fistula, periodontal tissue damage, diabetic non-healing wound, the result of trauma, or resulting from surgery. In some embodiments, the diabetic non-healing wound is a diabetic ulcer.

As used herein, "blood product" is understood to mean a composition derived from whole blood (e.g., autologous irradiated whole blood). For example, a blood product can include platelet-rich plasma. A blood product can be whole blood. In some cases, the platelet-rich plasma is enriched for a particular growth factor such as platelet derived growth factor (e.g., as a result of irradiation with light as disclosed herein).

As used herein, "PRP" is understood to mean platelet-rich plasma. Platelet-rich plasma can be isolated and characterized as set forth in, for instance, Cavallo et al., *BioMed Research International*, volume 2016, Article ID 6591717; and/or as set forth in Dhurat and Sukesh, *J. Cutan. Aesthet. Surg.* 2014 October-December; 7(4): 189-197, the contents of which are incorporated by reference in their entirety. As used herein, platelet-rich plasma can comprise platelets at a concentration of about $1.0\times10^5$ to about $1.0\times10^6$ platelets per $mm^3$.

As used herein, "PDGF" is understood to mean platelet derived growth factor. Written as [PDGF], it refers to the concentration of PDGF. PDGF is a growth factor that regulates cell growth and division. PDGF ligands act as dimers through two tyrosine kinase receptors, platelet derived growth factor receptor alpha (PDGFRα) and platelet derived growth factor receptor beta (PDGFRβ), to activate cellular responses to PDGF signaling. PDGF ligand monomeric subunits are encoded by platelet derived growth factor subunit A (PDGFA), platelet derived growth factor subunit B (PDGFB), platelet derived growth factor C (PDGFC) and platelet derived growth factor D (PDGFD). Known PDGF ligands include PDGF-AA, PDGF-BB, PDGF-CC. PDGF-DD and PDGF-AB. All PDGF signaling is envisaged as within the scope of the disclosure.

PDGF signals through the receptor tyrosine kinases PDGFRalpha and PDGFRbeta. It has been shown that PDGF-induced migration involves signaling pathways involving MEK/ERK, EGFR, Src, and PI3K/AKT (Kim et al.). PDGF-AA is commonly used to differentiate human pluripotent stem cell (hPSC)-derived neural progenitor cells into oligodendrocyte precursor cells.

Platelet-derived growth factor-BB (PDGF-BB) is one of the most abundant growth factors in platelet derived products and has been shown to stimulate regeneration after tissue injury.

Hair follicle regeneration is dependent on reciprocal signaling between epithelial cells and underlying mesenchymal cells within the dermal papilla. Hair follicle dermal stem cells reside within the hair follicle mesenchyme, self-renew in vivo, and function to repopulate the dermal papilla and regenerate the connective tissue sheath with each hair cycle. Platelet-derived growth factor signaling is crucial for hair follicle dermal stem cell function (Gonzalez et al., npj Regenerative Medicine volume 2, Article number: 11 (2017)).

Immature neurons from CNS stem cells proliferate in response to PDGF. PDGF acts as a mitogen in the early phase of stem cell differentiation to expand the pool of immature neurons (Erlandsson et al., J. Neuroscience 15 May 2001, 21 (10) 3483-3491). PDGF is also mitogenic for dermal and tendon fibroblasts, vascular smooth muscle cells, glial cells and chondrocytes. PDGF also interacts with Transforming Growth Factor-1 in accelerating wound healing.

As used herein, "VEGF" is understood to mean vascular endothelial growth factor. Written as [VEGF], it refers to the concentration of VEGF. VEGF is a family of growth factors involved in angiogenesis, amongst other functions. VEGF ligands include vascular endothelial growth factor A (VEGFA), vascular endothelial growth factor B (VEGFB), vascular endothelial growth factor C (VEGFC) and vascular endothelial growth factor D (VEGFD). VEGF receptors include fms related tyrosine kinase 1 (VEGFR1), kinase insert domain receptor (VEGFR2) and fms related tyrosine kinase 4 (VEGFR3). All VEGF signaling is envisaged as within the scope of the disclosure.

As used herein, "radiant exposure" or "fluence" is understood to mean the radiant energy of light received by a surface per unit area. Radiant exposure can be measured in units of joules per square centimeter ($J/cm^2$).

As used herein, the term "platelet-rich plasma" or "PRP" as used herein is a broad term which is used in its ordinary sense and is a concentration of platelets greater than the peripheral blood concentration suspended in a solution of plasma, or other excipient suitable for administration to a human or non-human animal including, but not limited to isotonic sodium chloride solution, physiological saline, normal saline, dextrose 5% in water, dextrose 10% in water, Ringer solution, lactated Ringer solution, Ringer lactate, Ringer lactate solution, and the like. PRP compositions may be an autologous preparation from whole blood taken from the subject to be treated or, alternatively, PRP compositions may be prepared from a whole blood sample taken from a single donor source or from whole blood samples taken from multiple donor sources. In general, PRP compositions comprise platelets at a platelet concentration that is higher than the baseline concentration of the platelets in whole blood.

In some embodiments, PRP compositions may further comprise WBCs at a WBC concentration that is higher than the baseline concentration of the WBCs in whole blood. As used herein, baseline concentration means the concentration of the specified cell type found in the patient's blood that would be the same as the concentration of that cell type found in a blood sample from that patient without manipulation of the sample by laboratory techniques such as cell sorting, centrifugation or filtration. Where blood samples are obtained from more than one source, baseline concentration means the concentration found in the mixed blood sample from which the PRP is derived without manipulation of the mixed sample by laboratory techniques such as cell sorting, centrifugation or filtration.

In some embodiments, PRP compositions comprise elevated concentrations of platelets and WBCs and lower levels of RBCs and hemoglobin relative to their baseline concentrations. In some embodiments, only the concentration of platelets is elevated relative to the baseline concentration. Some embodiments of the PRP composition comprise elevated levels of platelets and WBCs compared to baseline concentrations. In some embodiments, PRP compositions comprise elevated concentrations of platelets and lower levels of neutrophils relative to their baseline concentrations. Some embodiments of the PRP composition comprise elevated levels of platelets and neutrophil-depleted WBCs compared to their baseline concentrations. In some embodiments, the ratio of lymphocytes and monocytes to neutrophils is significantly higher than the ratios of their baseline concentrations.

The PRP formulation may include platelets at a level of between about 1.01 and about 2 times the baseline, about 2 and about 3 times the baseline, about 3 and about 4 times the baseline, about 4 and about 5 times the baseline, about 5 and about 6 times the baseline, about 6 and about 7 times the baseline, about 7 and about 8 times the baseline, about 8 and about 9 times the baseline, about 9 and about 10 times the baseline, about 11 and about 12 times the baseline, about 12 and about 13 times the baseline, about 13 and about 14 times the baseline, or higher. In some embodiments, the platelet concentration may be between about 4 and about 6 times the baseline. Typically, a microliter of whole blood comprises at least 140,000 to 150,000 platelets and up to 400,000 to 500,000 platelets. The PRP compositions may comprise about 500,000 to about 7,000,000 platelets per microliter. In some instances, the PRP compositions may comprise about 500,000 to about 700,000, about 700,000 to about 900,000, about 900,000 to about 1,000,000, about 1,000,000 to about 1,250,000, about 1,250,000 to about 1,500,000, about 1,500,000 to about 2,500,000, about 2,500,000 to about 5,000,000, or about 5,000,000 to about 7,000,000 platelets per microliter.

The PRP composition may be delivered as a liquid, a solid, a semi-solid (e.g., a gel), an inhalable powder, or some combination thereof. When the PRP is delivered as a liquid, it may comprise a solution, an emulsion, a suspension, etc. A PRP semi-solid or gel may be prepared by adding a clotting agent (e.g., thrombin, epinephrine, calcium salts) to the PRP. The gel may be more viscous than a solution and therefore may better preserve its position once it is delivered to target tissue. In some embodiments, the delivery to the target tissue can include delivery to a treatment area in the body as well as incorporation into cell cultures or suspensions as described herein. In some embodiments, the PRP composition is delivered without a clotting agent.

In some instances, it may be desirable to deliver the PRP composition as a liquid and have it gel or harden in situ. For example, the PRP compositions may include, for example, collagen, cyanoacrylate, adhesives that cure upon injection into tissue, liquids that solidify or gel after injection into tissue, suture material, agar, gelatin, light-activated dental composite, other dental composites, silk-elastin polymers, Matrigel® gelatinous protein mixture (BD Biosciences), hydrogels and/or other suitable biopolymers. Alternatively, the above-mentioned agents need not form part of the PRP mixture. For example, the above-mentioned agents may be delivered to the target tissue before or after the PRP has been delivered to the target tissue to cause the PRP to gel. In some embodiments, the PRP composition may harden or gel in response to one or more environmental or chemical factors such as temperature, pH, proteins, etc.

The PRP may be buffered using an alkaline buffering agent to a physiological pH. The buffering agent may be a biocompatible buffer such as HEPES, TRIS, monobasic phosphate, monobasic bicarbonate, or any suitable combination thereof that may be capable of adjusting the PRP to physiological pH between about 6.5 and about 8.0. In certain embodiments, the physiological pH may be from about 7.3 to about 7.5 and may be about 7.4. For example, the buffering agent may be an 8.4% sodium bicarbonate solution. In these embodiments, for each cc of PRP isolated from whole blood, 0.05 cc of 8.4% sodium bicarbonate may be added. In some embodiments, the syringe may be gently shaken to mix the PRP and bicarbonate.

As noted above, the PRP composition may comprise one or more additional agents, diluents, solvents, or other ingredients. Examples of the additional agents include, but are not limited to, thrombin, epinephrine, collagen, calcium salts, pH adjusting agents, materials to promote degranulation or preserve platelets, additional growth factors or growth factor inhibitors, NSAIDS, steroids, anti-infective agents, and mixtures and combinations of the foregoing.

In some embodiments, the PRP compositions may comprise a contrast agent for detection by an imaging technique such as X-rays, magnetic resonance imaging (MRI), or ultrasound. Examples of such contrast agents include, but are not limited to, X-ray contrast (e.g., IsoVue), MRI contrast (e.g., gadolinium), and ultrasound contrast.

Embodiments described herein utilize spectrally-controlled light to irradiate blood to produce blood products with desired characteristics, such as an enhanced concentration of a certain growth factor. As used herein, controlling the spectral content of light applied to a quantity of blood refers to controlling relative amounts of energy applied to the blood at various wavelengths. This may be accomplished, for example, by providing a light source that selectively increases the amount of light energy applied to the blood at a single wavelength or a relatively narrow band of wavelengths in addition to the light energy that is provided by uncontrolled ambient (e.g., broad spectrum) sources such that the spectral content of the aggregate light applied to the blood is controlled. In some embodiments, controlling the spectral content of light applied to a blood may include blocking ambient sources and limiting exposure of the blood to light produced from a spectrally-selective source, such as a solid-state light source (e.g., an LED or laser light source) that generates light with spectral power concentrated at a single wavelength or a relatively narrow band of wavelengths.

As used herein, "solid state light source" refers to light sources that employ one or more semiconductor devices that emit light when electrically activated. Such devices include, for example, light emitting diodes (LEDs), which are semiconductor devices that convert electrical current into light. Other solid-state devices, such as laser diodes can similarly be used to provide light. Commercially available solid-state lighting devices may include a semiconductor chip comprising one or more solid-state emitters (e.g., LEDs), along with subsidiary structures, such as coatings, lenses, leads and environmental packaging.

It will be appreciated that a solid-state lighting device, such as an LED or laser diode, may emit light limited to a single wavelength or concentrated in a relatively narrow range of wavelengths. For example, while a laser diode may emit light of a single wavelength, LEDs may emit light having a spectral distribution with power concentrated around a peak wavelength and falling off away from the peak wavelength. Therefore, even though an LED may have a pronounced peak wavelength, it may also produce light at attenuated levels at wavelengths away from the peak wavelength. A class of LEDs may be characterized by a nominal peak wavelength (e.g., 650 nm), but it will be appreciated that LEDs within a given group (e.g. a production lot) may have peak wavelengths that vary from this nominal peak wavelength within certain tolerances and, generally, spectral power distributions may vary slightly within the group. LEDs with different individual spectral power distributions may also be combined in a fixture or other device to produce a combined light output with particular spectral content that is an aggregate of the spectral contributions of the constituent members of the combination. Light produced by solid-state light sources may be coherent or non-coherent.

In various embodiments, LEDs and/or other solid-state light sources may be used to control spectral content of light that is applied to a quantity of blood to stimulate production of a growth factor or other blood component. For example, a concentration of a platelet-derived growth factor (PDGF) in a quantity of blood may be increased by controlled application of light in a wavelength range from about 600 nm to about 900 nm using a solid-state light source. Such a light source may be additive to existing ambient (e.g., generally white) light or the quantity of blood to be irradiated may be placed in an enclosure that substantially blocks ambient light such that the light applied to the quantity of blood is generally limited to that provided by the solid-state light source.

In some embodiments, a sample of blood is isolated from a subject and treated (e.g., by irradiating the sample with light). In some embodiments, the treatment with light can cause an increase in the concentration of growth factors in the blood or a resulting blood product, and this treated (i.e., irradiated) blood or blood product can be administered back to the subject.

The present disclosure teaches the administration of compositions comprising blood or blood products (e.g., platelet-rich plasma) to a subject. In some embodiments, the blood or blood products can promote tissue growth in the subject. For example, the compositions can promote the growth (e.g., regrowth) of hair in the subject.

The blood or blood products contemplated herein can be non-autologous blood or blood products. That is, in some embodiments, a subject can be administered blood or a blood product that has been irradiated with light to increase the concentration of certain growth factors and that has been derived from a different subject (e.g., a different individual). For instance, the blood or blood products can be homologous blood or blood products.

In some embodiments, the blood products disclosed herein (e.g., plasma such as platelet-rich plasma or whole blood) can be autologous samples. That is, a subject can be administered with blood or a blood product that was originally derived from that subject. In some embodiments, the autologous blood or blood product can contain increased concentrations of autologous growth factors such as platelet derived growth factor. Accordingly, in some embodiments, the present disclosure can reduce or eliminate the need to add exogenous growth factors such as platelet derived growth factor to a sample derived from a subject. This can help to reduce or eliminate the probability of an immune response (e.g., an adverse immune reaction) caused by the administration of non-autologous blood products described herein.

In some embodiments, blood products such as PRP comprise elevated concentrations of platelets and white blood cells (WBCs) and lower levels of red blood cells (RBCs) and hemoglobin relative to the baseline concentrations of these components in whole blood. In some embodiments, only the concentration of platelets is elevated relative to its baseline concentration in whole blood.

In some embodiments, the concentrations of platelets and WBCs are elevated relative to their baseline concentrations in whole blood. In some embodiments, the blood product compositions (e.g., PRP) comprise elevated concentrations of platelets and lower levels of neutrophils relative to their baseline concentrations in whole blood. In some embodiments, the blood products (e.g., PRP) comprise elevated levels of platelets and neutrophil-depleted WBCs compared to their baseline concentrations in whole blood. In some embodiments, the ratio of lymphocytes and monocytes to neutrophils in the blood products (e.g., PRP) is significantly higher than the ratios of their baseline concentrations in whole blood.

In some embodiments, the blood products described herein (e.g., platelet-rich plasma) can comprise platelets at a level of between about 1.01 and about 2 times the baseline in whole blood, about 2 and about 3 times the baseline, about 3 and about 4 times the baseline, about 4 and about 5 times the baseline; about 5 and about 6 times the baseline, about 6 and about 7 times the baseline, about 7 and about 8 times the baseline, about 8 and about 9 times the baseline, about 9 and about 10 times the baseline, about 11 and about 12 times the baseline, about 12 and about 13 times the baseline, about 13 and about 14 times the baseline, or higher. In some embodiments, the platelet concentration may be between about 4 and about 6 times the baseline. In some embodiments, a microliter of whole blood (e.g., un-irradiated whole blood) comprises at least 140,000 to 150,000 platelets and up to 400,000 to 500,000 platelets. In some embodiments, the blood products described herein (e.g., platelet-rich plasma) can comprise about 500,000 to about 7,000,000 platelets per microliter. In some embodiments, the blood products described herein (e.g., platelet-rich plasma) can comprise about 500,000 to about 700,000, about 700,000 to about 900,000, about 900,000 to about 1,000,000, about 1,000,000 to about 1,250,000, about 1,250,000 to about 1,500,000, about 1,500,000 to about 2,500,000, about 2,500,000 to about 5,000,000, or about 5,000,000 to about 7,000,000 platelets per microliter.

The white blood cell (WBC) concentration can be elevated in the blood products described herein (e.g., in PRP). For example, the WBC concentration can be between about 1.01 and about 2 times the baseline in whole blood, about 2 and about 3 times the baseline, about 3 and about 4 times the baseline, about 4 and about 5 times the baseline, about 5 and about 6 times the baseline, about 6 and about 7 times the baseline, about 7 and about 8 times the baseline, about 8 and about 9 times the baseline, about 9 and about 10 times the baseline, or higher. In some embodiments, the WBC count in a microliter of whole blood (e.g., un-irradiated whole blood) is about 4,100 to 4,500 and up to 10,900 to 11,000. The WBC count in a microliter of a composition of the present disclosure can be between about 8,000 and about 10,000; about 10,000 and about 15,000; about 15,000 and about 20,000; about 20,000 and about 30,000; about 30,000 and about 50,000; about 50,000 and about 75,000; and about 75,000 and about 100,000.

In whole blood (e.g., un-irradiated whole blood), the lymphocyte count can be between about 1,300 and 4,000 cells per microliter, the monocyte count can be between about 200 and 800 cells per microliter, and the eosinophil concentration can be about 40 to 400 cells per microliter. In the blood products disclosed herein (e.g., platelet-rich plasma), the monocyte concentration can be less than about 1,000 per microliter, between about 1,000 and about 5,000 per microliter, or greater than about 5,000 per microliter. The eosinophil concentration can be between about 200 and about 1,000 per microliter. In some variations, the eosinophil concentration can be less than about 200 per microliter or greater than about 1,000 per microliter.

In certain embodiments, the blood products (e.g., platelet-rich plasma compositions) disclosed herein can contain a specific concentration of neutrophils. The neutrophil concentration can vary between less than the baseline concentration of neutrophils (e.g., in un-irradiated whole blood) to eight times than the baseline concentration of neutrophils (e.g., in un-irradiated whole blood). In some embodiments, the blood products (e.g., platelet-rich plasma compositions) disclosed herein can include neutrophils at a concentration of 50-70%, 30-50%, 10-30%, 5-10%, 1-5%, 0.5-1%, 0.1-0.5% of levels of neutrophils found in whole blood or less. In some embodiments, neutrophil levels are depleted to 1% or less than that found in whole blood. In some variations, the neutrophil concentration can be between about 0.01 and about 0.1 times baseline in whole blood, about 0.1 and about 0.5 times baseline, about 0.5 and 1.0 times baseline, about 1.0 and about 2 times baseline, about 2 and about 4 times baseline, about 4 and about 6 times baseline, about 6 and about 8 times baseline, or higher. The neutrophil concentration can additionally or alternatively be specified relative to the concentration of the lymphocytes and/or the monocytes. One microliter of whole blood (e.g., un-irradiated whole blood) can comprise about 2,000 to 7,500 neutrophils. In some variations, the blood products (e.g., platelet-rich plasma compositions) disclosed herein can comprise neutrophils at a concentration of less than about 1,000 per microliter, about 1,000 to about 5,000 per microliter, about 5,000 to about 20,000 per microliter, about 20,000 to about 40,000 per microliter, or about 40,000 to about 60,000 per microliter. In some embodiments, neutrophils are eliminated or substantially eliminated. Means to deplete blood products, such as PRP, of neutrophils is known and discussed in U.S. Pat. No. 7,462,268, the contents of which are incorporated herein by reference.

In some embodiments, the blood products (e.g., platelet-rich plasma compositions) disclosed herein can comprise levels of platelets and white blood cells that are elevated compared to whole blood and in which the ratio of monocytes and/or lymphocytes to neutrophils is higher than in whole blood. In some embodiments, the ratio of monocytes and/or lymphocytes to neutrophils can serve as an index to determine if a blood product (e.g., PRP) formulation may be efficaciously used as a treatment for a particular disease or condition. Blood product (e.g., PRP) compositions in which the ratio of monocytes and/or lymphocytes to neutrophils is increased can be generated either by lowering neutrophils levels, or by maintaining neutrophil levels while increasing levels of monocytes and/or lymphocytes. In some embodiments, the blood products (e.g., platelet-rich plasma compositions) disclosed herein can comprise at least about 1.01 times the baseline concentration of platelets and at least about 1.01 times the baseline concentration of white blood cells wherein the neutrophil component is depleted at least 1% from baseline.

In some embodiments, the blood products (e.g., platelet-rich plasma compositions) disclosed herein can comprise a lower concentration of red blood cells (RBCs) and/or hemoglobin than the concentration in whole blood (e.g., un-irradiated whole blood). The RBC concentration can be between about 0.01 and about 0.1 times baseline in whole blood, about 0.1 and about 0.25 times baseline, about 0.25 and about 0.5 times baseline, or about 0.5 and about 0.9 times baseline. The hemoglobin concentration can be depressed and in some variations may be about 1 g/dl or less, between about 1 g/dl and about 5 g/dl, about 5 g/dl and about 10 g/dl, about 10 g/dl and about 15 g/dl, or about 15 g/dl and about 20 g/dl. In some embodiments, whole blood (e.g., un-irradiated whole blood) drawn from a male patient can have an RBC count of at least 4,300,000 to 4,500,000 and up to 5,900,000 to 6,200,000 per microliter whereas whole blood (e.g., un-irradiated whole blood) from a female patient can have an RBC count of at least 3,500,000 to 3,800,000 and up to 5,500,000 to 5,800,000 per microliter. These RBC counts can correspond to hemoglobin levels of at least 132 g/L to 135 g/L and up to 162 g/L to 175 g/L for men and at least 115 g/L to 120 g/L and up to 152 g/L to 160 g/L for women.

Samples of blood can be isolated from a subject by standard methods known in the art. For example, blood can be drawn from a patient by inserting a needle into a subject's vein and collecting the blood in a blood tube.

The present disclosure provides methods of increasing the concentration of growth factors such as PDGF in a sample of blood or blood product by irradiating whole blood with light. Once the whole blood has been irradiated, the whole blood can be separated into its components to produce blood products (e.g., fractions of the whole blood such as platelet-rich plasma).

As set forth in the Examples below, the present disclosure teaches that irradiating whole blood with light can increase the concentration of growth factors in the blood compared to irradiating fractions of blood (e.g., platelet-rich plasma) with light at the same wavelength and same fluence. In other words, irradiating whole blood before it is separated leads to different concentrations of growth factors in the resulting blood products (e.g., platelet-rich plasma) than irradiating fractions of whole blood.

For example, as set forth in Example 1, whole blood and platelet-rich plasma were both irradiated with light at a wavelength of 850 nm and a fluence of 10 J/cm$^2$. As set forth in FIG. 5, the concentration of platelet derived growth factor in the sample of irradiated whole blood increased over 250% compared with a sample of whole blood that had not been irradiated with light. In contrast, the sample of irradiated platelet-rich plasma experienced a negligible change in the amount of platelet derived growth factor compared with a sample of platelet-rich plasma that had not been irradiated with light. Accordingly, in some embodiments, the present disclosure provides for irradiating whole blood with light prior to separating the whole blood into its components (e.g., by centrifugation).

In some embodiments, the light source used to irradiate the whole blood can be incoherent light (e.g., light produced from an LED or OLED source). In some embodiments, the light source used to irradiate the whole blood can be coherent light (e.g., light produced by a laser).

The present disclosure provides for controlling the optical transmittance of the light (e.g., LED light) through a sample of whole blood during irradiation. In some embodiments, at least a portion of the light is scattered or absorbed by the whole blood. In some embodiments, the transmittance of light through the whole blood is at least about 10%, at least about 20%, at least about 30%, at least about 40%, at least about 50%, at least about 60%, at least about 70%, at least about 80%, at least about 90%, or at least about 100%.

In some embodiments, whole blood can be irradiated with light at a range or plurality of wavelengths to increase the concentration of growth factors in the blood. For example, in some embodiments, whole blood can be irradiated with light comprising the visible spectrum (e.g., substantially all of the visible spectrum or a portion of the visible spectrum). In some embodiments, the whole blood can be irradiated with light comprising the ultraviolet portion of the electromagnetic spectrum (e.g., substantially all of the ultraviolet spectrum or a portion of the ultraviolet spectrum). In some embodiments, the whole blood can be irradiated with light comprising the infrared portion of the electromagnetic spectrum (e.g., substantially all of the infrared spectrum or a portion of the infrared spectrum). In some embodiments, whole blood can be irradiated with a portion of the ultraviolet, visible, and/or infrared spectrum. Thus, in some embodiments, whole blood can be irradiated with multiple wavelengths of light simultaneously, e.g., by irradiating the whole blood with every wavelength within a particular range. For example, whole blood can be irradiated with all of the wavelengths in the visible spectrum, and/or all of the wavelengths in the infrared spectrum.

In some embodiments, the present disclosure teaches irradiating whole blood with light at particular wavelengths. For example, in some embodiments, the concentration of a particular growth factor can be modulated (e.g., increased) by irradiating the whole blood with light at a particular wavelength.

For instance, as set forth in Example 2, the concentration of platelet derived growth factor in a resulting sample of platelet-rich plasma increased as the whole blood from which the platelet-rich plasma was derived was irradiated with light at longer wavelengths (i.e., at lower energy). Specifically, Example 2 shows that irradiating whole blood at wavelengths of 420 nm and 530 nm led to slight (i.e., less than 50%) increases in the concentration of platelet derived growth factor in the resulting sample of platelet-rich plasma, compared with whole blood that had not been irradiated with light. However, as whole blood was irradiated with light at increasingly longer wavelengths, the concentration of platelet derived growth factor in the resulting platelet-rich plasma increased. For example, irradiating whole blood with light at 597 nm led to an increase of platelet derived growth factor in the resulting platelet-rich plasma of about 75% compared with the platelet-rich plasma derived from un-irradiated whole blood. Similarly, irradiating whole blood at a wavelength of about 660 nm led to an increase of platelet derived growth factor of about 250% in the platelet-rich plasma compared to platelet-rich plasma derived from whole blood that had not been irradiated with light. Irradiating whole blood at a wavelength of about 850 nm led to an increase of platelet derived growth factor of about 275% in the platelet-rich plasma compared to platelet-rich plasma derived from whole blood that had not been irradiated with light. Accordingly, irradiating whole blood with a particular wavelength of light can produce platelet-rich plasma that is enriched in a particular growth factor (e.g., platelet derived growth factor).

In some embodiments, the present disclosure teaches irradiating whole blood with light at multiple wavelengths to modulate (e.g., increase or decrease) the concentration of multiple growth factors simultaneously. For example, as set forth in Example 2 and without wishing to be bound by theory, the concentration of platelet derived growth factor in platelet-rich plasma can be increased by irradiating the whole blood from which the platelet-rich plasma is derived with light at a wavelength of at least about 850 nm. However, as set forth in Example 2 and without wishing to be bound by theory, irradiating whole blood with light at 850 nm did not have a substantial effect on the concentration of other growth factors (e.g., VEGF). Accordingly, in some embodiments, the concentration of other growth factors in platelet-rich plasma can be modulated (e.g., increased or decreased) by irradiating whole blood with light at other wavelengths prior to isolating the platelet-rich plasma from the irradiated whole blood.

In some embodiments, and without wishing to be bound by theory, the present disclosure contemplates that two or more growth factors (e.g., platelet derived growth factor and an additional growth factor) can be simultaneously modulated by irradiating whole blood with multiple specific wavelengths of light at once. Additional growth factors in PRP include, but are not limited to, transforming growth factor beta (TGF-β), Wingless/Int-1 (Wnt) family proteins, RNA-binding protein (FBF), epidermal growth factor (EGF), fibroblast growth factor 2 (FGF-2), keratinocyte growth factor (KGF or FGF-7), insulin-like growth factor (IGF), VEGF, transforming growth-factor-beta (TGF-b), and beta catenin. In some embodiments, the additional growth factor comprises a cytokine. In some embodiments, the Wnt family protein is Wnt4.

The spectral content of light used to irradiate whole blood can be controlled by a variety of techniques known in the art, such as optical filters, and prisms. In some embodiments, light-emitting diodes (LEDs) can be used to emit light predominantly at a particular wavelength to irradiate the whole blood. In some embodiments, a laser can be used to emit light at a particular wavelength to irradiate the whole blood.

Accordingly, in some embodiments, whole blood can be irradiated at a wavelength (e.g., a specific wavelength) of at least about 400 nm; at least about 450 nm; at least about 500 nm; at least about 550 nm; at least about 600 nm; at least about 650 nm; at least about 700 nm; at least about 750 nm; at least about 800 nm; at least about 850 nm; at least about 900 nm; at least about 950 nm; at least about 1000 nm; or at least about 1500 nm.

FIG. 1 illustrates operations according to some embodiments. A spectral content of light applied to a quantity of blood is controlled to enhance a growth factor, such as PDGF (block 110). A plasma product is extracted from the processed quantity of blood (block 120). A composition derived from the plasma product is administered to a subject (block 130).

Figure 2:
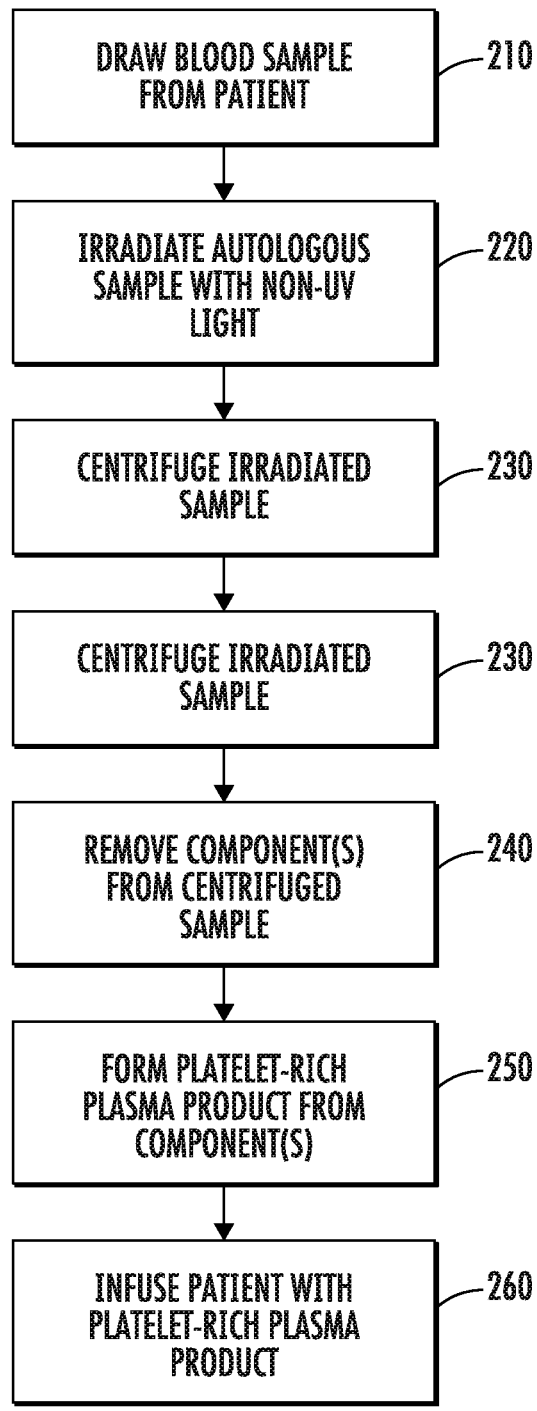
FIG. 2 is a diagram illustrating operations for fabricating an irradiated platelet rich blood product (PRP) and treating a subject with light irradiated PRP according to further embodiments.

FIG. 2 illustrates operations according to further embodiments. A blood sample is drawing from a patient (block 210). The autologous sample is radiated with non-UV light (block 220). The irradiated sample is then centrifuged and one or more components is extracted from the centrifuged sample (blocks, 230, 240). A PRP is formed from the extracted one or more components (block 250). The patient is infused with the PRP (block 260).

Figure 3:
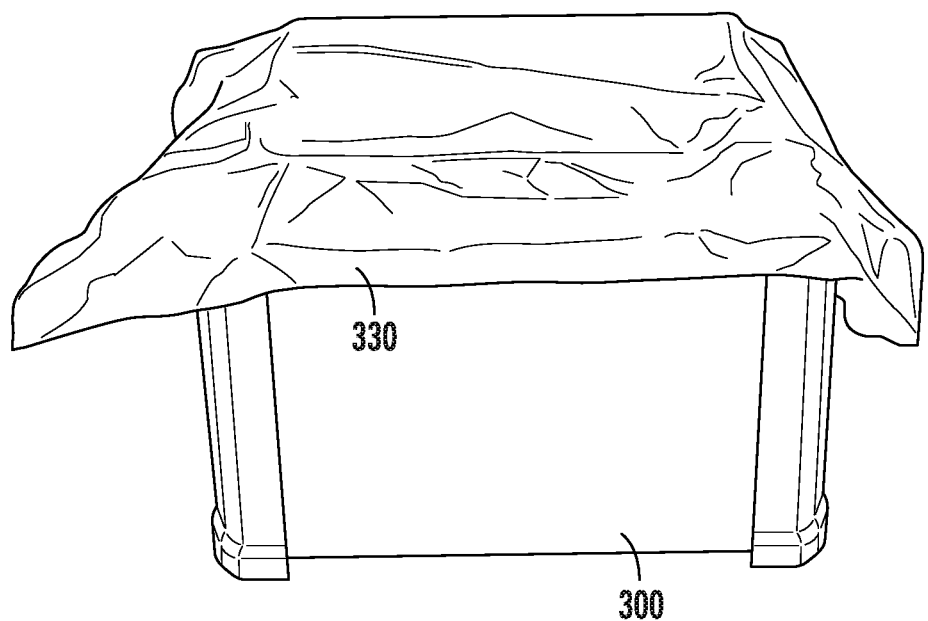
FIG. 3 is a side view of an apparatus for irradiating blood with spectrally selective light according to some embodiments.
Figure 4:
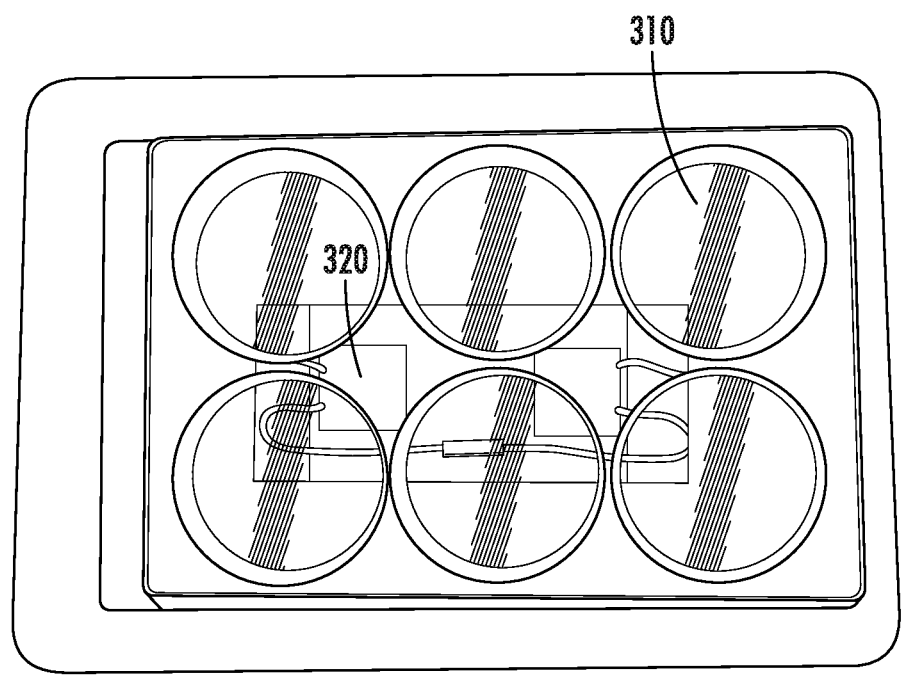
FIG. 4 is a top view of the apparatus of FIG. 3 with a top cover removed.

FIGS. 3 and 4 illustrate an apparatus for irradiating blood to produce a PRP as explained for the Examples below. The apparatus includes an enclosure 300 configured to house at least one vessel, here shown as test wells 310 of a transparent plate that are configured to hold samples of whole blood. The test wells 310 overlie two LED light sources 320 that are used to irradiate blood contained in the test wells 310. The enclosure 300 is covered by a cover, here shown as a foil 330, to block application of ambient light to the blood in the test wells 310 while the LEDs 310 apply light with a non-ambient spectral power distribution to blood in the test wells 310.

Figure 5:
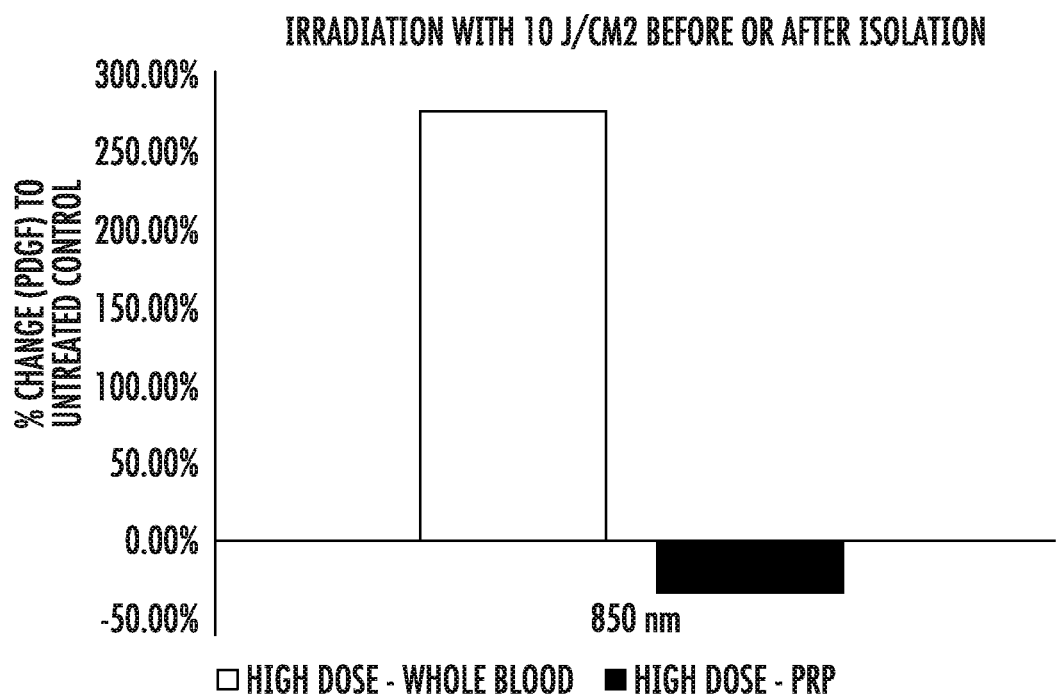
FIG. 5 is a plot illustrating a change in the concentration of platelet derived growth factor (PDGF) in a platelet rich blood product (PRP) fabricated according to some embodiments.

FIGS. 5-12 show results for blood products produced by irradiating a sample of whole blood with spectrally-controlled light. FIG. 5 is a plot illustrating a change in the concentration of platelet derived growth factor (PDGF) in platelet rich blood products (PRP) is process dependent. Whole blood (left bar), or isolated PRP (right bar) were irradiated with 850 nanometer (nm) light at 10 J/cm² either before or after isolation of PRP, and the percent increase of PDGF relative to an untreated control was determined. When $CaCl_2$ was added to PRP as a control, the change in PDGF concentration was 142%. When $CaCl_2$ was added to whole blood and then PRP was isolated, the change in PDGF concentration was 41.4%.

Figure 6:
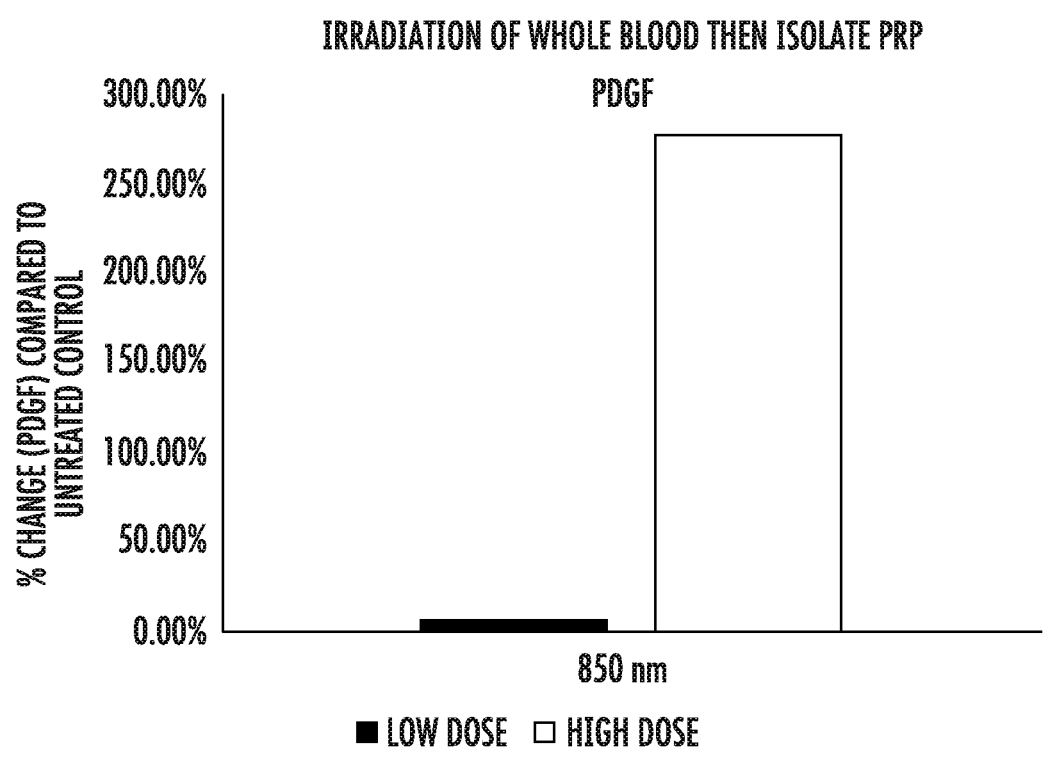
FIG. 6 is a plot illustrating a change in PDGF in a PRP fabricated according to further embodiments.

FIG. 6 is a plot illustrating that the change in [PDGF] in PRP in response to light irradiation of whole blood is dose dependent. Whole blood was irradiated with a low dose of 1 J/cm² (left bar) or high dose of 10 J/cm² (right bar) of 850 nm light, the PRP was isolated, and the percent increase of PDGF relative to an untreated control was determined. When $CaCl_2$ was added to whole blood as a control, and then PRP was isolated, the change in PDGF concentration was 41.4%.

Figure 7:
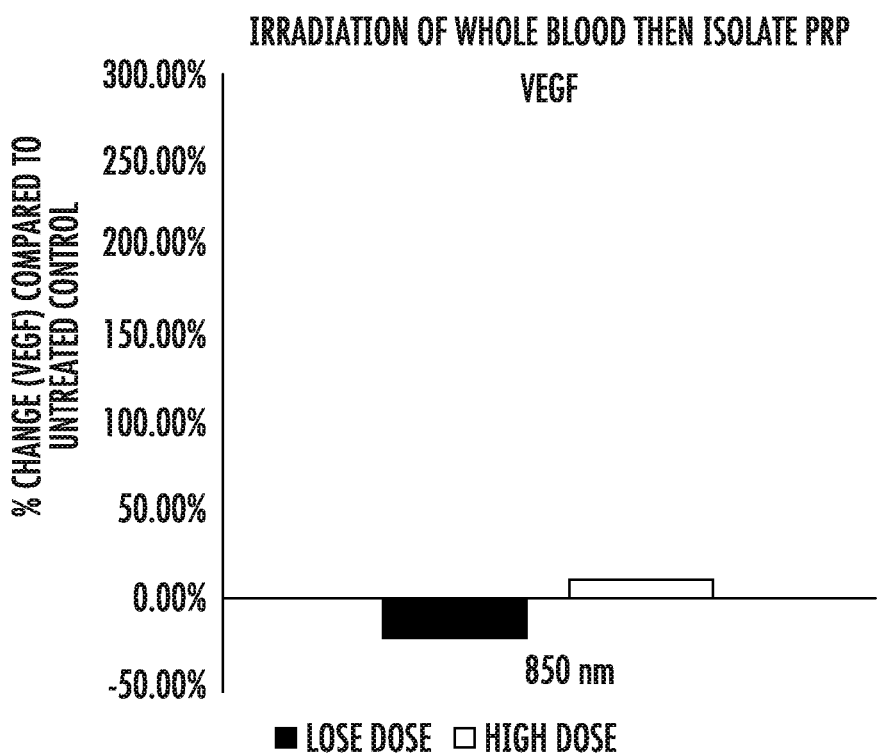
FIG. 7 is a plot illustrating levels of VEGF in a PRP in response to irradiation of whole blood with 850 nm light.

FIG. 7 is a plot illustrating that levels of VEGF in PRP do not increase in response to irradiation with 850 nm light. Whole blood was irradiated with a low dose of 1 J/cm² (left bar) or high dose of 10 J/cm² (right bar) of 850 nm light, PRP was isolated, and the change in [VEGF] relative to an untreated control was determined. When $CaCl_2$ was added to PRP as a control, the change in VEGF concentration was 46.7%. When $CaCl_2$ was added to whole blood and then PRP was isolated, the change in VEGF concentration was 28.8%.

Figure 8:
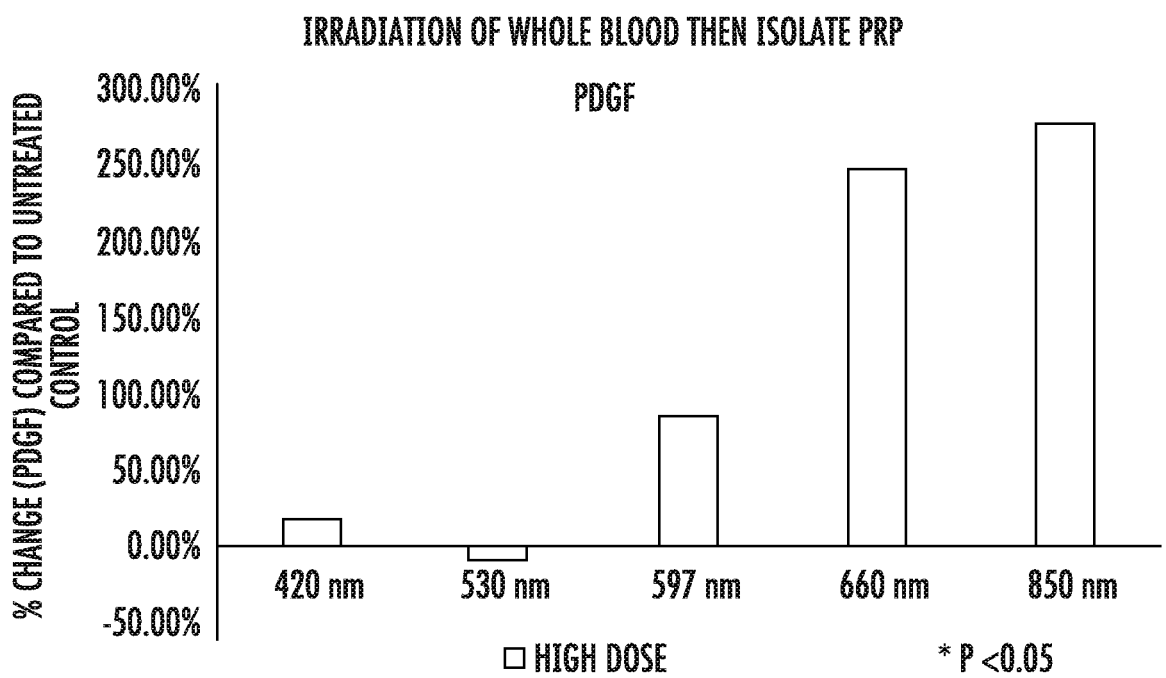
FIG. 8 is a plot illustrating a percent change in PDGF in a PRP fabricated from light irradiated whole blood based upon the wavelength of light used to irradiate the whole blood.

FIG. 8 is a plot illustrating that the percent change in [PDGF] in PRP from light irradiated whole blood is dependent upon the wavelength of light used to irradiate the whole blood. Decreasing energy at fixed fluence levels leads to increased PDGF. Whole blood was irradiated at wavelengths of 420 nm, 530 nm, 597 nm, 660 nm and 850 nm at a high dose of 10 J/cm², PRP was isolated, and the percent increase of PDGF relative to an untreated control was determined. When $CaCl_2$ was added to whole blood as a control, and then PRP was isolated, the change in PDGF concentration was 41.4%. (*) indicates increases with $p<0.05$.

Figure 9:
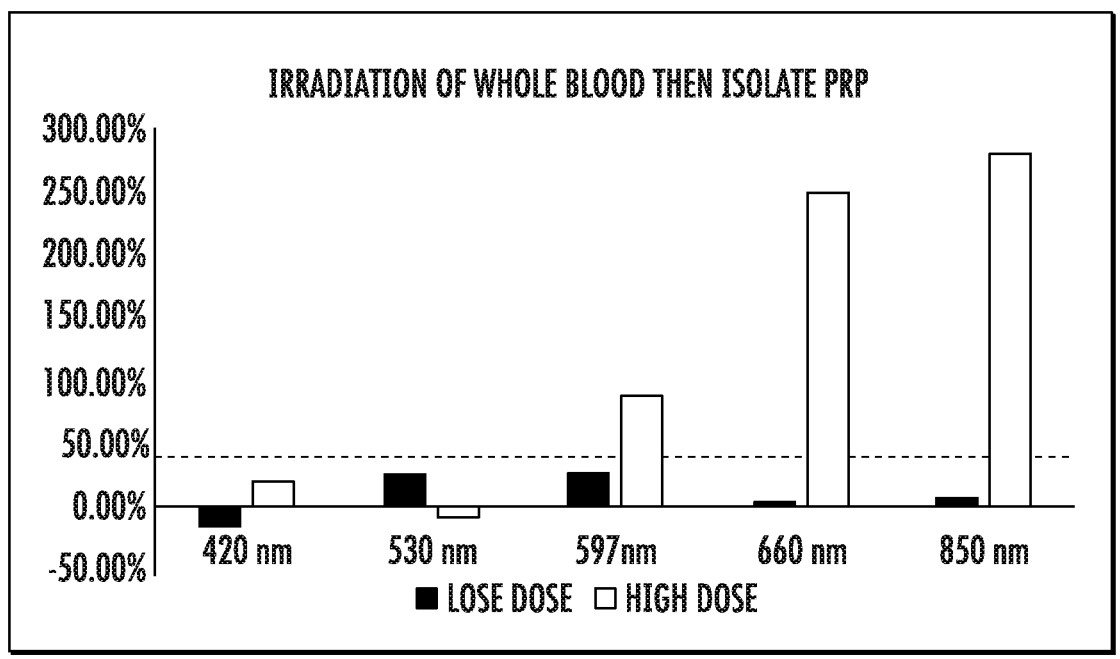
FIG. 9 is a plot illustrating a percent change of PDGF in a PRP relative to an untreated control when whole blood is irradiated at various wavelengths and radiant exposure levels prior to isolation of the PRP.

FIG. 9 is a plot illustrating the percent change of [PDGF] in PRP relative to an untreated control when whole blood was irradiated with 420 nm, 530 nm, 597 nm, 660 nm or 850 nm light at a low dose of 1 J/cm² (left bars) or a high dose of 10 J/cm² (right bars) prior to isolation of PRP. The dashed line indicates the increase in PDGF shown in a control when $CaCl_2$ was added to whole blood and PRP isolated. (*) indicates statistically significant increases with $p<0.05$.

Figure 10:
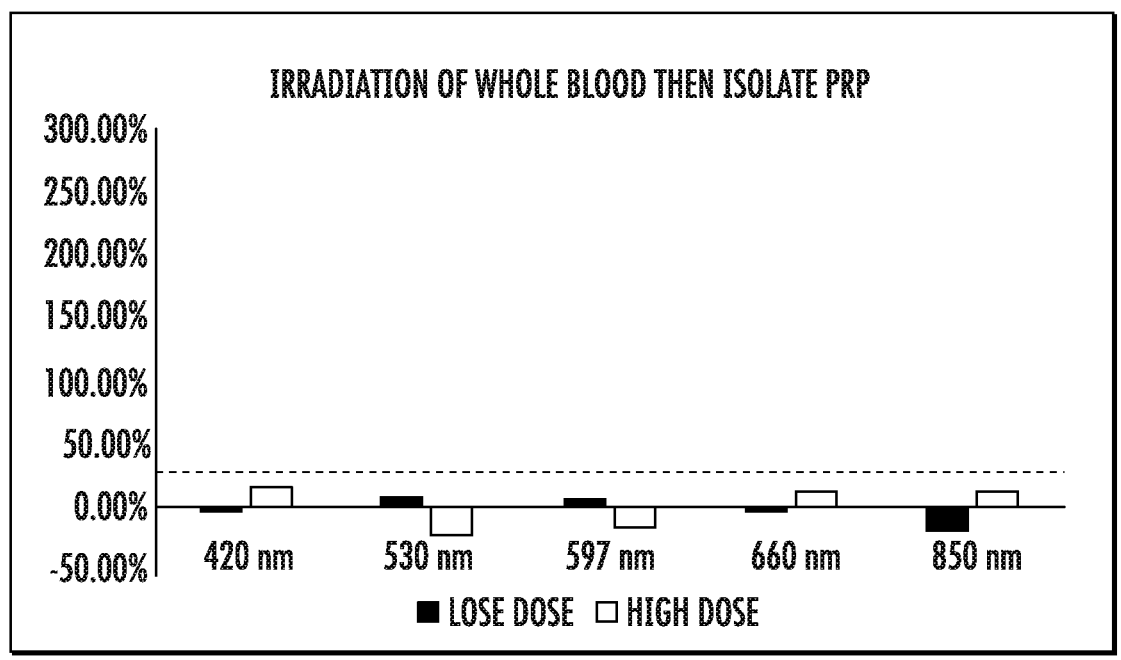
FIG. 10 is a plot illustrating a percent change in VEGF in a PRP relative to an untreated control when whole blood was irradiated at various wavelengths and doses.

FIG. 10 is a plot illustrating the percent change in [VEGF] in PRP relative to an untreated control when whole blood was irradiated with 420 nm, 530 nm, 597 nm, 660 nm or 850 nm light at a low dose of 1 J/cm² (left bars) or a high dose of 10 J/cm² (right bars) prior to isolation of PRP. The dashed line indicates the increase in VEGF shown in a control when $CaCl_2$ was added to whole blood PRP isolated.

Figure 11:
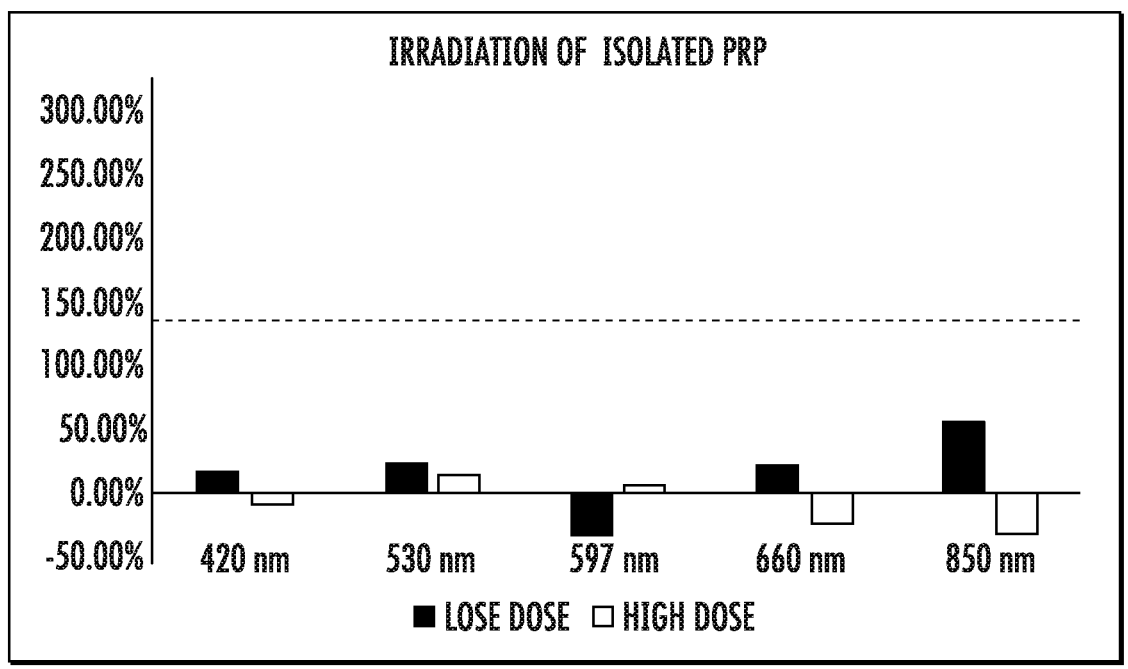
FIG. 11 is a plot illustrating a percent change in PDGF in a PRP relative to an untreated control when the PRP was irradiated at various wavelengths and doses.

FIG. 11 is a plot illustrating the percent change in [PDGF] in PRP relative to an untreated control when PRP was irradiated with 420 nm, 530 nm, 597 nm, 660 nm or 850 nm light at a low dose of 1 J/cm² (left bars) or a high dose of 10 J/cm² (right bars). The dashed line indicates the increase in PDGF shown in a control when $CaCl_2$ was added to PRP.

Figure 12:
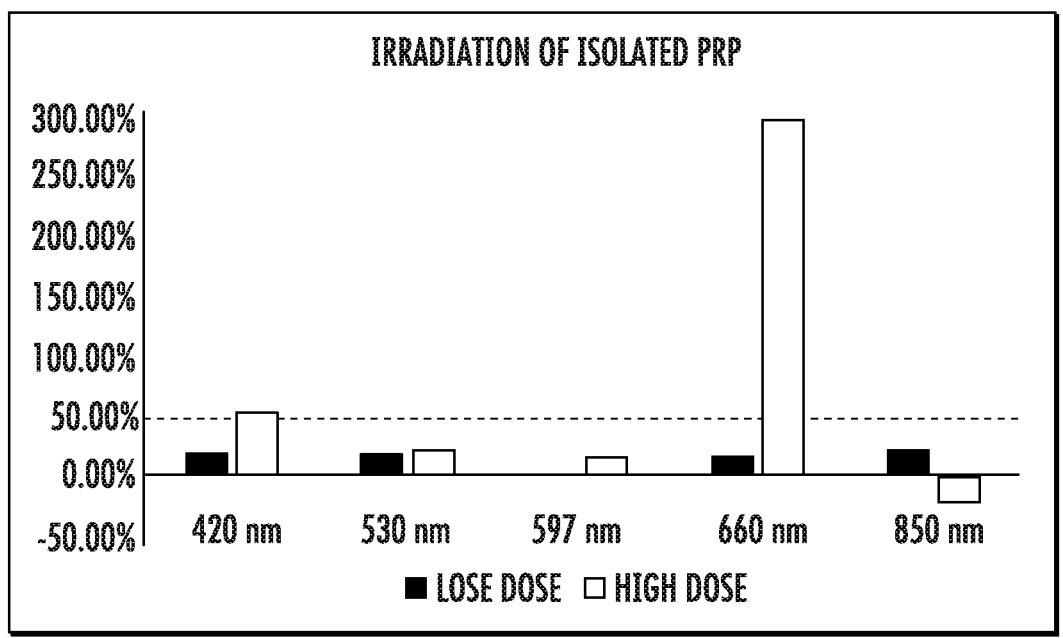
FIG. 12 is a plot illustrating a percent change in VEGF in a PRP relative to an untreated control when the PRP was irradiated at various wavelengths and doses.

FIG. 12 shows the percent change in [VEGF] in PRP relative to an untreated control when PRP was irradiated with 420 nm, 530 nm, 597 nm, 660 nm or 850 nm light at a low dose of 1 J/cm² (left bars) or a high dose of 10 J/cm² (right bars). The dashed line indicates the increase in VEGF shown in a control when $CaCl_2$) was added to PRP. The large % increase at 660 nm is due to a single outlying value in one of three replicates and is not statistically significant.

Figure 13:
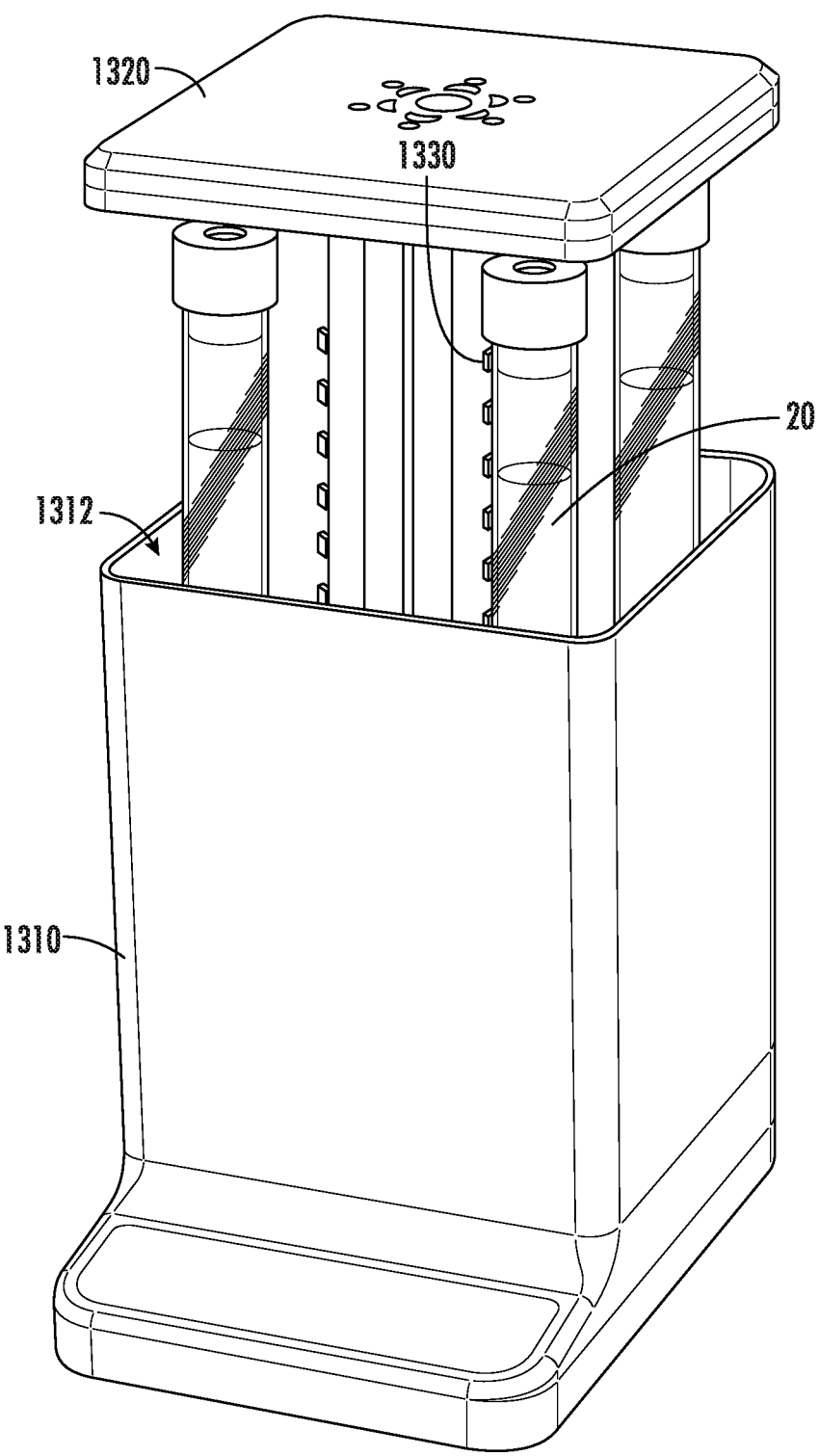
FIG. 13 is a perspective view of a blood processing apparatus according to some embodiments.

It will be appreciated that FIGS. 3 and 4 illustrate an apparatus for processing blood with spectrally-controlled light to modulate various growth factors. FIG. 13 illustrates an example implementation of a processing apparatus employing similar principles according to further embodiments. The apparatus includes an enclosure 1310 having a compartment 1312 therein configured to receive one or more vessels, e.g., tubular vials 20 that contain blood for treatment. A removable rack 1320 is configured to support the vials 20 and has a multiple arrays of LED light sources 1330 that are configured to apply spectrally selective light to the blood in the vials 20 when the rack 1320 is inserted into the compartment 1312. When the rack 1320 is fully inserted in the enclosure 1310, the apparatus blocks application of ambient light to the blood in the vials 20 such that irradiation of the blood will be limited to the spectrally-controlled light produced by the LED light sources 1330. The processed blood in the vials 20 may be further processed (e.g., centrifuged) and plasma products extracted therefrom for use in compositions that may be administered to a subject.

In some embodiments, the concentration of growth factors (e.g., platelet derived growth factor) in blood or a blood product such as platelet-rich plasma can be modulated (e.g., increased or decreased) by irradiating whole blood at various radiant exposures of light. For example, as set forth in Example 2 and FIG. 5, irradiating whole blood at a wavelength of about 850 nm led to an increase of platelet derived growth factor of about 275% in the resulting platelet-rich plasma when the whole blood was irradiated at a fluence of 10 J/cm². However, irradiating whole blood at the same wavelength of about 850 nm did not lead to a significant increase of platelet derived growth factor (i.e., less than about 10%) in the resulting platelet-rich plasma when the whole blood was irradiated at a fluence of 1 J/cm².

Accordingly, in some embodiments, the present disclosure teaches irradiating whole blood with various radiant exposures of light to modulate the concentrations of various growth factors in the resulting blood and blood product (e.g., platelet-rich plasma).

Accordingly, in some embodiments, whole blood can be irradiated at a radiant exposure of at least about 1 J/cm²; at least about 2 J/cm²; at least about 3 J/cm²; at least about 4 J/cm²; at least about 5 J/cm²; at least about 6 J/cm²; at least about 7 J/cm²; at least about 8 J/cm²; at least about 9 J/cm²; at least about 10 J/cm²; at least about 15 J/cm²; at least about 20 J/cm²; or at least about 25 J/cm².

In some embodiments, both the radiant energy and the wavelength of light used to irradiate whole blood can be adjusted to modulate the concentration of a growth factor (e.g., platelet-rich plasma) in the blood or a resulting blood product (e.g., platelet-rich plasma).

Accordingly, in some embodiments, whole blood is irradiated at a wavelength of about 600 nm and a radiant exposure of about 1 J/cm². In some embodiments, whole blood is irradiated at a wavelength of about 600 nm and a radiant exposure of about 2 J/cm². In some embodiments, whole blood is irradiated at a wavelength of about 600 nm and a radiant exposure of about 3 J/cm². In some embodiments, whole blood is irradiated at a wavelength of about 600 nm and a radiant exposure of about 4 J/cm². In some embodiments, whole blood is irradiated at a wavelength of about 600 nm and a radiant exposure of about 5 J/cm². In some embodiments, whole blood is irradiated at a wavelength of about 600 nm and a radiant exposure of about 6 J/cm². In some embodiments, whole blood is irradiated at a wavelength of about 600 nm and a radiant exposure of about 7 J/cm². In some embodiments, whole blood is irradiated at a wavelength of about 600 nm and a radiant exposure of about 8 J/cm². In some embodiments, whole blood is irradiated at a wavelength of about 600 nm and a radiant exposure of about 9 J/cm². In some embodiments, whole blood is irradiated at a wavelength of about 600 nm and a radiant exposure of about 10 J/cm². In some embodiments, whole blood is irradiated at a wavelength of about 600 nm and a radiant exposure of about 15 J/cm². In some embodiments, whole blood is irradiated at a wavelength of about 600 nm and a radiant exposure of about 20 J/cm². In some embodiments, whole blood is irradiated at a wavelength of about 600 nm and a radiant exposure of about 25 J/cm². In any of the above-embodiments, the whole blood can be irradiated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, or at least about 15 minutes, In some embodiments, whole blood is irradiated at a wavelength of about 650 nm and a radiant exposure of about 1 J/cm². In some embodiments, whole blood is irradiated at a wavelength of about 650 nm and a radiant exposure of about 2 J/cm². In some embodiments, whole blood is irradiated at a wavelength of about 650 nm and a radiant exposure of about 3 J/cm². In some embodiments, whole blood is irradiated at a wavelength of about 650 nm and a radiant exposure of about 4 J/cm². In some embodiments, whole blood is irradiated at a wavelength of about 650 nm and a radiant exposure of about 5 J/cm². In some embodiments, whole blood is irradiated at a wavelength of about 650 nm and a radiant exposure of about 6 J/cm². In some embodiments, whole blood is irradiated at a wavelength of about 650 nm and a radiant exposure of about 7 J/cm². In some embodiments, whole blood is irradiated at a wavelength of about 650 nm and a radiant exposure of about 8 J/cm². In some embodiments, whole blood is irradiated at a wavelength of about 650 nm and a radiant exposure of about 9 J/cm². In some embodiments, whole blood is irradiated at a wavelength of about 650 nm and a radiant exposure of about 10 J/cm². In some embodiments, whole blood is irradiated at a wavelength of about 650 nm and a radiant exposure of about 15 J/cm². In some embodiments, whole blood is irradiated at a wavelength of about 650 nm and a radiant exposure of about 20 J/cm². In some embodiments, whole blood is irradiated at a wavelength of about 650 nm and a radiant exposure of about 25 J/cm². In any of the above-embodiments, the whole blood can be irradiated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, or at least about 15 minutes, In some embodiments, whole blood is irradiated at a wavelength of about 700 nm and a radiant exposure of about 1 J/cm². In some embodiments, whole blood is irradiated at a wavelength of about 700 nm and a radiant exposure of about 2 J/cm². In some embodiments, whole blood is irradiated at a wavelength of about 700 nm and a radiant exposure of about 3 J/cm². In some embodiments, whole blood is irradiated at a wavelength of about 700 nm and a radiant exposure of about 4 J/cm². In some embodiments, whole blood is irradiated at a wavelength of about 700 nm and a radiant exposure of about 5 J/cm². In some embodiments, whole blood is irradiated at a wavelength of about 700 nm and a radiant exposure of about 6 J/cm². In some embodiments, whole blood is irradiated at a wavelength of about 700 nm and a radiant exposure of about 7 J/cm². In some embodiments, whole blood is irradiated at a wavelength of about 700 nm and a radiant exposure of about 8 J/cm². In some embodiments, whole blood is irradiated at a wavelength of about 700 nm and a radiant exposure of about 9 J/cm². In some embodiments, whole blood is irradiated at a wavelength of about 700 nm and a radiant exposure of about 10 J/cm². In some embodiments, whole blood is irradiated at a wavelength of about 700 nm and a radiant exposure of about 15 J/cm². In some embodiments, whole blood is irradiated at a wavelength of about 700 nm and a radiant exposure of about 20 J/cm². In some embodiments, whole blood is irradiated at a wavelength of about 700 nm and a radiant exposure of about 25 J/cm². In any of the above-embodiments, the whole blood can be irradiated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, or at least about 15 minutes, In some embodiments, whole blood is irradiated at a wavelength of about 750 nm and a radiant exposure of about 1 J/cm². In some embodiments, whole blood is irradiated at a wavelength of about 750 nm and a radiant exposure of about 2 J/cm². In some embodiments, whole blood is irradiated at a wavelength of about 750 nm and a radiant exposure of about 3 J/cm². In some embodiments, whole blood is irradiated at a wavelength of about 750 nm and a radiant exposure of about 4 J/cm². In some embodiments, whole blood is irradiated at a wavelength of about 750 nm and a radiant exposure of about 5 J/cm². In some embodiments, whole blood is irradiated at a wavelength of about 750 nm and a radiant exposure of about 6 J/cm². In some embodiments, whole blood is irradiated at a wavelength of about 750 nm and a radiant exposure of about 7 J/cm². In some embodiments, whole blood is irradiated at a wavelength of about 750 nm and a radiant exposure of about 8 J/cm². In some embodiments, whole blood is irradiated at a wavelength of about 750 nm and a radiant exposure of about 9 J/cm². In some embodiments, whole blood is irradiated at a wavelength of about 750 nm and a radiant exposure of about 10 J/cm². In some embodiments, whole blood is irradiated at a wavelength of about 750 nm and a radiant exposure of about 15 J/cm². In some embodiments, whole blood is irradiated at a wavelength of about 750 nm and a radiant exposure of about 20 J/cm². In some embodiments, whole blood is irradiated at a wavelength of about 750 nm and a radiant exposure of about 25 J/cm². In any of the above-embodiments, the whole blood can be irradiated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, or at least about 15 minutes.

In some embodiments, whole blood is irradiated at a wavelength of about 800 nm and a radiant exposure of about 1 J/cm². In some embodiments, whole blood is irradiated at a wavelength of about 800 nm and a radiant exposure of about 2 J/cm². In some embodiments, whole blood is irradiated at a wavelength of about 800 nm and a radiant exposure of about 3 J/cm². In some embodiments, whole blood is irradiated at a wavelength of about 800 nm and a radiant exposure of about 4 J/cm². In some embodiments, whole blood is irradiated at a wavelength of about 800 nm and a radiant exposure of about 5 J/cm². In some embodiments, whole blood is irradiated at a wavelength of about 800 nm and a radiant exposure of about 6 J/cm². In some embodiments, whole blood is irradiated at a wavelength of about 800 nm and a radiant exposure of about 7 J/cm². In some embodiments, whole blood is irradiated at a wavelength of about 800 nm and a radiant exposure of about 8 J/cm². In some embodiments, whole blood is irradiated at a wavelength of about 800 nm and a radiant exposure of about 9 J/cm². In some embodiments, whole blood is irradiated at a wavelength of about 800 nm and a radiant exposure of about 10 J/cm². In some embodiments, whole blood is irradiated at a wavelength of about 800 nm and a radiant exposure of about 15 J/cm². In some embodiments, whole blood is irradiated at a wavelength of about 800 nm and a radiant exposure of about 20 J/cm². In some embodiments, whole blood is irradiated at a wavelength of about 800 nm and a radiant exposure of about 25 J/cm². In any of the above-embodiments, the whole blood can be irradiated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, or at least about 15 minutes.

In some embodiments, whole blood is irradiated at a wavelength of about 850 nm and a radiant exposure of about 1 J/cm². In some embodiments, whole blood is irradiated at a wavelength of about 850 nm and a radiant exposure of about 2 J/cm². In some embodiments, whole blood is irradiated at a wavelength of about 850 nm and a radiant exposure of about 3 J/cm². In some embodiments, whole blood is irradiated at a wavelength of about 850 nm and a radiant exposure of about 4 J/cm². In some embodiments, whole blood is irradiated at a wavelength of about 850 nm and a radiant exposure of about 5 J/cm². In some embodiments, whole blood is irradiated at a wavelength of about 850 nm and a radiant exposure of about 6 J/cm². In some embodiments, whole blood is irradiated at a wavelength of about 850 nm and a radiant exposure of about 7 J/cm². In some embodiments, whole blood is irradiated at a wavelength of about 850 nm and a radiant exposure of about 8 J/cm². In some embodiments, whole blood is irradiated at a wavelength of about 850 nm and a radiant exposure of about 9 J/cm². In some embodiments, whole blood is irradiated at a wavelength of about 850 nm and a radiant exposure of about 10 J/cm². In some embodiments, whole blood is irradiated at a wavelength of about 850 nm and a radiant exposure of about 15 J/cm². In some embodiments, whole blood is irradiated at a wavelength of about 850 nm and a radiant exposure of about 20 J/cm². In some embodiments, whole blood is irradiated at a wavelength of about 850 nm and a radiant exposure of about 25 J/cm². In any of the above-embodiments, the whole blood can be irradiated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, or at least about 15 minutes.

In some embodiments, whole blood is irradiated at a wavelength of about 900 nm and a radiant exposure of about 1 J/cm². In some embodiments, whole blood is irradiated at a wavelength of about 900 nm and a radiant exposure of about 2 J/cm². In some embodiments, whole blood is irradiated at a wavelength of about 900 nm and a radiant exposure of about 3 J/cm². In some embodiments, whole blood is irradiated at a wavelength of about 900 nm and a radiant exposure of about 4 J/cm². In some embodiments, whole blood is irradiated at a wavelength of about 900 nm and a radiant exposure of about 5 J/cm². In some embodiments, whole blood is irradiated at a wavelength of about 900 nm and a radiant exposure of about 6 J/cm². In some embodiments, whole blood is irradiated at a wavelength of about 900 nm and a radiant exposure of about 7 J/cm². In some embodiments, whole blood is irradiated at a wavelength of about 900 nm and a radiant exposure of about 8 J/cm². In some embodiments, whole blood is irradiated at a wavelength of about 900 nm and a radiant exposure of about 9 J/cm². In some embodiments, whole blood is irradiated at a wavelength of about 900 nm and a radiant exposure of about 10 J/cm². In some embodiments, whole blood is irradiated at a wavelength of about 900 nm and a radiant exposure of about 15 J/cm². In some embodiments, whole blood is irradiated at a wavelength of about 900 nm and a radiant exposure of about 20 J/cm². In some embodiments, whole blood is irradiated at a wavelength of about 900 nm and a radiant exposure of about 25 J/cm². In any of the above-embodiments, the whole blood can be irradiated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, or at least about 15 minutes.

In some embodiments, whole blood is irradiated at a wavelength of about 950 nm and a radiant exposure of about 1 J/cm². In some embodiments, whole blood is irradiated at a wavelength of about 950 nm and a radiant exposure of about 2 J/cm². In some embodiments, whole blood is irradiated at a wavelength of about 950 nm and a radiant exposure of about 3 J/cm². In some embodiments, whole blood is irradiated at a wavelength of about 950 nm and a radiant exposure of about 4 J/cm². In some embodiments, whole blood is irradiated at a wavelength of about 950 nm and a radiant exposure of about 5 J/cm². In some embodiments, whole blood is irradiated at a wavelength of about 950 nm and a radiant exposure of about 6 J/cm². In some embodiments, whole blood is irradiated at a wavelength of about 950 nm and a radiant exposure of about 7 J/cm². In some embodiments, whole blood is irradiated at a wavelength of about 950 nm and a radiant exposure of about 8 J/cm². In some embodiments, whole blood is irradiated at a wavelength of about 950 nm and a radiant exposure of about 9 J/cm². In some embodiments, whole blood is irradiated at a wavelength of about 950 nm and a radiant exposure of about 10 J/cm². In some embodiments, whole blood is irradiated at a wavelength of about 950 nm and a radiant exposure of about 15 J/cm². In some embodiments, whole blood is irradiated at a wavelength of about 950 nm and a radiant exposure of about 20 J/cm². In some embodiments, whole blood is irradiated at a wavelength of about 950 nm and a radiant exposure of about 25 J/cm². In any of the above-embodiments, the whole blood can be irradiated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, or at least about 15 minutes.

In some embodiments, whole blood is irradiated at a wavelength of about 1000 nm and a radiant exposure of about 1 J/cm². In some embodiments, whole blood is irradiated at a wavelength of about 1000 nm and a radiant exposure of about 2 J/cm². In some embodiments, whole blood is irradiated at a wavelength of about 1000 nm and a radiant exposure of about 3 J/cm². In some embodiments, whole blood is irradiated at a wavelength of about 1000 nm and a radiant exposure of about 4 J/cm². In some embodiments, whole blood is irradiated at a wavelength of about 1000 nm and a radiant exposure of about 5 J/cm². In some embodiments, whole blood is irradiated at a wavelength of about 1000 nm and a radiant exposure of about 6 J/cm². In some embodiments, whole blood is irradiated at a wavelength of about 1000 nm and a radiant exposure of about 7 J/cm². In some embodiments, whole blood is irradiated at a wavelength of about 1000 nm and a radiant exposure of about 8 J/cm². In some embodiments, whole blood is irradiated at a wavelength of about 1000 nm and a radiant exposure of about 9 J/cm². In some embodiments, whole blood is irradiated at a wavelength of about 1000 nm and a radiant exposure of about 10 J/cm². In some embodiments, whole blood is irradiated at a wavelength of about 1000 nm and a radiant exposure of about 15 J/cm². In some embodiments, whole blood is irradiated at a wavelength of about 1000 nm and a radiant exposure of about 20 J/cm². In some embodiments, whole blood is irradiated at a wavelength of about 1000 nm and a radiant exposure of about 25 J/cm². In any of the above-embodiments, the whole blood can be irradiated for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, or at least about 15 minutes.

Although the FDA may not permit the combination of stem cells with exogenous growth factors, it can be advantageous to pre-treat a patient with compounds that optimize the PRP that will be combined, in some embodiments, with stem cells.

Granulocyte-colony stimulating factor (GCSF) can mobilize cells from bone marrow including platelets. Pretreating patients with GCSF will enhance the value of PRP by increasing the number of platelets and other reparative cells. This may be especially true in patients with low platelet counts or in older patients that have lower cell counts. GCSF or other molecules that mobilize cells are given once, twice or many times prior to drawing whole blood from any source as described above. A preferred protocol would be to give GCSF for several days prior to the PRP isolation.

One specific method is to administer granulocyte colony-stimulating factor (G-CSF, also known as pegfilgrastim) or any other molecule that stimulates the production of stem cells by the body to a patient prior to the preparation of PRP. 5-50 micrograms per kilogram per day is administered to a patient for 1-10 days. PRP is then prepared from whole blood of the patient. The whole blood may be from any source including bone marrow and spleen. In a preferred embodiment, 10 micrograms per kilogram per day of G-CSF is administered subcutaneously to a patient for 1-10 days. PRP is then prepared from whole blood of the patient from any source including bone marrow or the spleen. Additional medications or newer molecules that stimulate blood or stem cell production could be added or substituted. In some embodiments, a molecule is administered to stimulate endogenous production of desired cells prior to preparing the PRP or bone marrow concentrate to be used therapeutically or for the reprogramming, proliferation, or differentiation of cells. Examples of other potential molecules include but are not limited to: plerixafor, sargramostim, gamma-tocotrienol, vitamin E and ancestim. As science evolves, newer molecules that help mobilize desired cells will be developed. It is anticipated by this filing that these newer molecules would be included in the list that could be administered prior to the production of PRP or other bioactive blood fractions.

By giving a patient such a mobilizing drug prior to preparing PRP, it should be noted that the composition will change compared to without such a cell mobilization drug.

In alternate embodiments, the molecule, such as G-CSF is administered at the same time that the PRP is administered or the molecule, such as G-CSF, is administered after the administration of PRP for a period to be determined depending on the treatment. For example, for treatment of a connective tissue injury, G-CSF with or without PRP may be administered over a period of weeks of months on a regular basis such as once a week, twice a week, three times per week or more as determined by the medical practitioner. In some embodiments, the molecule, such as G-CSF is administered before blood is taken from the patient for isolation of PRP for a period of 1-10 days as well as at the same time as administration of PRP to the patient and/or after administration of PRP as described above. PRP contains cytokines such as SDF-1 that are chemoattractive for stem cells. In some embodiments, the use of GCSF would enhance the value of the PRP treatment by mobilizing more cells.

In some embodiments, the light, administered at wavelengths between 600 and 1500 nm, is antimicrobial. Nitric oxide is known to be antimicrobial. The precise mechanisms by which nitric oxide (NO) kills or inhibits the replication of a variety of intracellular pathogens is not completely understood. However, it appears that the cysteine proteases are targeted (Saura et al., Immunity, Volume 10, Issue 1, 1 Jan. 1999, Pages 21-28). NO S-nitrosylates the cysteine residue in the active site of certain viral proteases, inhibiting protease activity and interrupting the viral life cycle. Since cysteine proteases are critical for virulence or replication of many viruses, bacteria, and parasites, NO production and release can be used to treat microbial infections. Accordingly, in some embodiments, light is administered at wavelengths effective for enhancing endogenous NO production and/or release. These wavelengths are discussed in more detail below. The photoinitiated release of endogenous stores of nitric oxide ("NO") effectively regenerates "gaseous" (or unbound) nitric oxide that was autoxidized into nitrosative intermediates and were bound covalently in the body in an "bound" state. By stimulating release of nitric oxide from endogenous stores, nitric oxide may be maintained in a gaseous state for an extended duration and/or a spatial zone of nitric oxide release may be expanded.

Nitric oxide is endogenously stored on a variety of nitrosated biochemical structures. Upon receiving the required excitation energy, both nitroso and nitrosyl compounds undergo hemolytic cleavage of S—N, N—N, or M-N bonds to yield free radical nitric oxide. Nitrosothiols and nitrosamines are photoactive and can be phototriggered to release nitric oxide by wavelength specific excitation. The effect of light at certain wavelengths in the production and/or release of nitric oxide is described in U.S. Pat. No. 10,525,275, the contents of which are hereby incorporated by reference.

Specific wavelengths of visible light are also known to destroy bacteria, mold and fungi cells as well. Intense blue light, typically between 400 and 500 nm, and preferably at around 400-430 nm, such as 415 nm, is purportedly better than red light for killing bacteria. (Lubart, R et al. "A possible mechanism for the bactericidal effect of visible light." Laser therapy vol. 20, 1 (2011): 17-22. doi:10.5978/islsm.20.17). In some embodiments, in addition to light administered at wavelengths of 600-1500 nm to increase the concentration of one or more growth factors, light is also administered at wavelengths which are antimicrobial, to sterilize and/or disinfect the blood products, such as PRP, before it is reinjected into the patient.

As set forth herein, whole blood can be irradiated with light to increase the concentration of various growth factors in the whole blood and resulting blood products (e.g., platelet-rich plasma) derived from the whole blood. As set forth herein, whole blood can be irradiated prior to separation of the whole blood into its constituent components.

Irradiated whole blood can be separated according to standard techniques. For example, irradiated whole blood can be centrifuged (e.g., at about 3500 RPM for about 10 minutes) to separate the whole blood into various components such as plasma, red blood cells (RBCs), white blood cells, and platelets.

In some embodiments, whole blood isolated from a subject can be treated with an anticoagulant. In some embodiments, whole blood isolated from a subject can be treated with calcium chloride (i.e., $CaCl_2$). Without wishing to be bound by theory, the addition of calcium chloride to whole blood can increase the concentration of certain growth factors (e.g., platelet derived growth factor) in the whole blood. Accordingly, the methods described herein (i.e., irradiating whole blood with light) can be used to increase the concentration of growth factors found in the whole blood or resulting blood products (e.g., platelet-rich plasma) relative to un-irradiated blood that is treated with calcium chloride.

In one embodiment, whole blood and/or blood products are treated with a combination of calcium chloride and irradiation, to have a combined enhancement of the concentration of one or more growth factors.

In some embodiments the step of isolating a sample of platelet-rich plasma from a sample of irradiated whole blood comprises: centrifuging the sample of irradiated whole blood to separate the components of the whole blood; removing a portion of platelet-poor plasma; re-suspending the platelets in the remaining amount of platelet-poor plasma to give a sample of platelet-rich plasma; and separating the platelet-rich plasma from the remaining components of the whole blood.

In some embodiments, the step of centrifuging the irradiated whole blood can be conducted at about 3500 RPM for about 10 minutes.

In some embodiments, centrifuging a sample of whole blood can separate the constituents of whole blood based on density. Without wishing to be bound by theory, in some embodiments the top layer of centrifuged (i.e., separated) blood can comprise mostly platelet-poor plasma; the next layer can comprise mostly platelets and white blood cells (i.e., the buffy coat); and the bottom layer can comprise mostly red blood cells.

Accordingly, the step of removing a portion of platelet-poor plasma can comprise simply decanting a portion of the platelet-poor plasma or withdrawing the platelet-poor plasma through a needle.

With a portion of the platelet-poor plasma removed, the platelets in the buffy coat (which were not removed when the portion of platelet-poor plasma was removed) can be re-suspended in the remaining platelet-poor plasma. In this way, without wishing to be bound by theory, the plasma can become platelet-rich plasma, because the total number of platelets that were present in the initial sample of whole blood can be re-suspended in a smaller volume of plasma than was present in the initial sample of whole blood.

In some embodiments, the resulting sample of platelet-rich plasma can be separated from the remaining components of the separated whole blood (e.g., from the red blood cells) by decanting the platelet-rich plasma or withdrawing the platelet-rich plasma through a needle.

In some embodiments, the sample of platelet-rich plasma can be isolated from irradiated whole blood within about 24 hours of irradiating the whole blood. In some embodiments, the sample of platelet-rich plasma can be isolated from irradiated whole blood within about 12 hours of irradiating the whole blood. In some embodiments, the sample of platelet-rich plasma can be isolated from irradiated whole blood within about 6 hours of irradiating the whole blood. In some embodiments, the sample of platelet-rich plasma can be isolated from irradiated whole blood within about 1 hour of irradiating the whole blood. In some embodiments, the sample of platelet-rich plasma can be isolated from irradiated whole blood within about 30 minutes of irradiating the whole blood. In some embodiments, the sample of platelet-rich plasma can be isolated from irradiated whole blood within about 20 minutes of irradiating the whole blood. In some embodiments, the sample of platelet-rich plasma can be isolated from irradiated whole blood within about 10 minutes of irradiating the whole blood. In some embodiments, the sample of platelet-rich plasma can be isolated from irradiated whole blood within about 5 minutes of irradiating the whole blood. In some embodiments, the sample of platelet-rich plasma can be isolated from irradiated whole blood within about 1 minute of irradiating the whole blood.

In some embodiments, compositions may include irradiated whole blood or blood products, such as PRP.

PRP may be delivered as a liquid, a solid, a semi-solid (e.g., a gel), an inhalable powder, or some combination thereof. When the PRP is delivered as a liquid, it may comprise a solution, an emulsion, a suspension, etc. A PRP semi-solid or gel may be prepared by adding a clotting agent (e.g., thrombin, epinephrine, calcium salts) to the PRP. The gel may be more viscous than a solution and therefore may better preserve its position once it is delivered to target tissue. In some embodiments, the delivery to the target tissue can include delivery to a treatment area in the body as well as incorporation into cell cultures or suspensions as described herein. In some embodiments, the PRP composition is delivered without a clotting agent.

In some instances, it may be desirable to deliver the PRP composition as a liquid and have it gel or harden in situ. For example, the PRP compositions may include, for example, collagen, cyanoacrylate, adhesives that cure upon injection into tissue, liquids that solidify or gel after injection into tissue, suture material, agar, gelatin, light-activated dental composite, other dental composites, silk-elastin polymers, Matrigel® gelatinous protein mixture (BD Biosciences), hydrogels and/or other suitable biopolymers. Alternatively, the above-mentioned agents need not form part of the PRP mixture. For example, the above-mentioned agents may be delivered to the target tissue before or after the PRP has been delivered to the target tissue to cause the PRP to gel. In some embodiments, the PRP composition may harden or gel in response to one or more environmental or chemical factors such as temperature, pH, proteins, etc.

The PRP may be buffered using an alkaline buffering agent to a physiological pH. The buffering agent may be a biocompatible buffer such as HEPES, TRIS, monobasic phosphate, monobasic bicarbonate, or any suitable combination thereof that may be capable of adjusting the PRP to physiological pH between about 6.5 and about 8.0. In certain embodiments, the physiological pH may be from about 7.3 to about 7.5 and may be about 7.4. For example, the buffering agent may be an 8.4% sodium bicarbonate solution. In these embodiments, for each cc of PRP isolated from whole blood, 0.05 cc of 8.4% sodium bicarbonate may be added. In some embodiments, the syringe may be gently shaken to mix the PRP and bicarbonate.

As noted above, the PRP composition may comprise one or more additional agents, diluents, solvents, or other ingredients. Examples of the additional agents include, but are not limited to, thrombin, epinephrine, collagen, calcium salts, pH adjusting agents, materials to promote degranulation or preserve platelets, additional growth factors or growth factor inhibitors, NSAIDS, steroids, anti-infective agents, and mixtures and combinations of the foregoing.

In some embodiments, the PRP compositions may comprise a contrast agent for detection by an imaging technique such as X-rays, magnetic resonance imaging (MRI), or ultrasound. Examples of such contrast agents include, but are not limited to, X-ray contrast (e.g., IsoVue), MRI contrast (e.g., gadolinium), and ultrasound contrast.

In some embodiments, the compositions further comprise stem cells, which can be embryonic stem cells, non-embryonic (adult) stem cells, and induced pluripotent stem cells (iPSCs). The stem cells can be derived, for example, from adipose tissue, bone marrow, peripheral blood, and combinations thereof.

In addition to stem cells, the compositions can further include human growth hormone, analogs thereof, or compounds which increase the production and/or release of human growth hormone.

Exogenous growth factors can also be added.

The present disclosure teaches the preparation of autologous blood or blood products (e.g., platelet-rich plasma) that are enriched in certain growth factors such as platelet derived growth factor. The autologous blood or blood products (e.g., platelet-rich plasma) can be used for a variety of therapeutic applications. For example, in some embodiments, autologous platelet-rich plasma can be administered to a subject to promote tissue regeneration. For example, autologous platelet-rich plasma can be administered to a subject to treat conditions such as tendonitis and osteoarthritis.

In further examples, the autologous blood or blood products (PRP) can be used to treat wound or tissue healing for example traumatic or surgical wounds such in the fitting and/or holding and/or sealing of native or prosthetic grafts (e.g. skin, bone grafts and/or dental prostheses or implants or the like, including also the graft donor site), vasculitis, ulcers such as diabetic neuropathic ulcers or decubitus sores, radiodermatitis (e.g. after irradiation on an epidermoidal skin carcinoma) or sun damage, or for closing fistulas.

In still further examples, the autologous blood or blood products (PRP) can be used to treat cardiac disorders, cardiac regeneration such as in the treatment of heart failure, chronic cardiac failure, ischemic and non-ischemic cardiac failure and cardiomyopathy.

In still further examples, the autologous blood or blood products (PRP) can be used to treat urinary and/or anal incontinence, reflux oesophagitis and/or gastro-oesophageal reflux disorder.

In still further examples, the autologous blood or blood products (PRP) can be used to treat skin damages, such as in skin damaged by radiations (radiodermatitis or sun damaged skin), aged skins or burned skins and/or in the amelioration of facial wrinkles, rhytids, acne (especially after dermabrasion treatment), burns, rubella or small pox scars, vitiligo, lipoatrophy or lipodystrophy, Kaposi's sarcoma, skin skeloids or Dupuytren's palmar fibromatosis and/or in skin rejuvenation treatments.

In still further examples, the autologous blood or blood products (PRP) can be used to treat lipoatrophy such as in HIV/AIDS patients and in other congenital hemiatrophy of the face, such as congenital cartilage nose atrophy.

In still further examples, the autologous blood or blood products (PRP) can be used to treat bone, cartilage and articular disorders such as chondral damage, arthritis, cartilage and/or bone injury such as deep cartilage damage and/or erosion and/or arthroscopy, torn tendon and rotator cuff in shoulder.

In still further examples, the autologous blood or blood products (PRP) can be used to treat hematological diseases such as Thalassemia.

In still further examples, the autologous blood or blood products (PRP) can be used to treat corneal disorders such as dry eye syndrome; corneal opacity such as those caused by chemical burns, affliction by Steven's Johnson syndrome; scarring of the cornea and corneal ulcers.

In still further examples, the autologous blood or blood products (PRP) can be used to treat peripheral nerve damage, nerve suture and spinal cord injury.

In some embodiments, the autologous blood products disclosed herein (e.g., platelet-rich plasma enriched in platelet derived growth factor) can be used for cosmetic uses. For example, the autologous blood products disclosed herein can be used to promote hair growth in a subject. For example, the autologous blood products disclosed herein can increase hair growth by at least about 10%, at least about 20%, at least about 30%, at least about 40%, at least about 50%, at least about 60%, at least about 70%, at least about 80%, at least about 90%, or at least about 100%. The treatment can be combined with phototherapy, for example, using light in the red and/or blue wavelengths, particularly wavelengths, as described herein, which promote the production and/or release of endogenous nitric oxide.

In some embodiments, the autologous blood products disclosed herein can be used to reduce scar tissue in a subject. The autologous blood products disclosed herein can reduce scar tissue by at least about 10%, at least about 20%, at least about 30%, at least about 40%, at least about 50%, at least about 60%, at least about 70%, at least about 80%, at least about 90%, or at least about 100%.

In some embodiments, the autologous blood products disclosed herein can be used to reduce skin wrinkles in a subject. The autologous blood products disclosed herein can reduce skin wrinkles by at least about 10%, at least about 20%, at least about 30%, at least about 40%, at least about 50%, at least about 60%, at least about 70%, at least about 80%, at least about 90%, or at least about 100%.

In some embodiments, the autologous blood products disclosed herein can be used to reduce skin fine lines in a subject. The autologous blood products disclosed herein can reduce skin fine lines by at least about 10%, at least about 20%, at least about 30%, at least about 40%, at least about 50%, at least about 60%, at least about 70%, at least about 80%, at least about 90%, or at least about 100%.

In some embodiments, the autologous blood products disclosed herein can be used to increase skin elasticity in a subject. The autologous blood products disclosed herein can increase skin elasticity by at least about 10%, at least about 20%, at least about 30%, at least about 40%, at least about 50%, at least about 60%, at least about 70%, at least about 80%, at least about 90%, or at least about 100%.

In some embodiments, the autologous blood products disclosed herein can be administered (e.g., injected) into a subject's face, scalp, dermis, epidermis, wrinkles, forehead, nose, penis, or vagina. In some embodiments, the autologous blood products disclosed herein can be administered (e.g., injected) directly to a subject's scar or injury.

In some embodiments, the blood products can be administered to a subject in need thereof topically, transdermally, buccally, sublingually, intraperitoneally, subcutaneously, subungually, transcranially, intramuscularly, intra-articularly, intravenously, intrapleurally, intrathecally and/or parenterally. In some embodiments, topical administration comprises administration to the eye (e.g., as an eye drop).

In some embodiments, administration (e.g., injection) can be carried out with a local anesthetic. For example, the local anesthetic can be lidocaine, prilocaine, tetracaine, TAC, benzocaine, chloroprocaine, cocaine, cyclomethycaine, dimethocaine (larocaine), piperocaine, propoxycaine, procaine (novocaine), proparacaine, tetracaine (amethocaine), propranolol, articaine, bupivacaine, cinchocaine (dibucaine), etidocaine, levobupivacaine, lidocaine (lignocaine), mepivacaine, prilocaine, ropivacaine, or trimecaine.

The present invention will be better understood with reference to the following non-limiting examples.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments, and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1: Irradiation of Whole Blood and Platelet Rich Plasma (PRP) with Select Wavelengths and Doses of Light Study Design Human blood was drawn and PRP or whole blood exposed to LEDs of various wavelengths for roughly 2-minute exposures. Exposed whole blood samples were spun down into PRP and both sets of samples were incubated for approximately 21 hours. Positive controls were generated through the addition of a 2.28M $CaCl_2$) solution. Each sample was performed in triplicate, and levels of PDGF and VEGF were measured with the selected ELISAs (VEGF-A and PDGF-AA, see Example 2).

Methodology

One subject was consented, completed some basic demographic and medical history data and had 100 mL of whole blood drawn via 22 gauge needles into 8.5 mL tubes with anticoagulant included. PRP or whole blood was allocated with 30 mL designated to be spun immediately into PRP. The remaining whole blood (80 mL) were placed in 4.5 mL aliquots into a single well of a 6 well culture dish for exposure (see FIG. 4). These wells were stored in a 37 degree cell culture incubator while the PRP was generated.

There were 12 plates in total: (a) 420 nm/9 mL total (4.5 mL low power plate/4.5 mL high power plate); (b) 530 nm/9 mL total (4.5 mL low power plate/4.5 mL high power plate); (c) 660 nm/9 mL total (4.5 mL low power plate/4.5 mL high power plate); (d) 597 nm/9 mL total (4.5 mL low power plate/4.5 mL high power plate); (e) 850 nm/9 mL total (4.5 mL low power plate/4.5 mL high power plate); (f) untreated (Untx)/Dark Control 4.5 mL (only one plate needed) and (g) Positive control 4.5 mL (only one plate needed).

30 mL of whole blood were left in the collection tubes and spun down to prepare plasma. The initial spin was for 10 minutes @ 1,500 relative centrifugal force (rcf). Upon completion of this spin, the plasma was not fully separated and appeared to be cloudy. A second spin 10 minutes was carried out. At completion of this second spin, the blood was still not clearly separated, so a final spin of 15 minutes @2100 rcf was completed. This brought about a clear separation and 1.5 mL (double the amount anticipated) of PRP was aliquoted into a single well of a 6 well cell culture dish for light-emitting diode (LED) exposure.

As with the whole blood, there were a total of 12 plates: (a) 420 nm/1.5 mL total (750 uL low power plate/750 uL high power plate); (b) 530 nm/1.5 mL total (750 uL low power plate/750 uL high power plate); (c) 660 nm/1.5 mL total (750 uL low power plate/750 uL high power plate); (d) 597 nm/1.5 mL total (750 uL low power plate/750 uL high power plate); (e) 850 nm/1.5 mL total (750 uL low power plate/750 uL high power plate); (f) Untreated (Untx)/Dark Control 750 uL (only one plate needed); (g) Positive control 750 uL (only one plate needed).

Experiment Performance

Two LED exposure systems were set up as shown in FIGS. 3 and 4. In brief, a LED bar was placed with LEDs 320 face up on a table. A Biobox enclosure 300 was placed on top of the LED bar 320 and centered. 6 well plates 310 were placed over the LEDs 320 and covered with foil 330 to prevent light contamination. A fan was placed approximately 1.5 inches away, with air flowing over the metal fins of the LED bar. LEDs were attached to a power supply, voltage was set at 30V and current at 140 mA. The same orientation of the plate in the LED set up was used for all testing. To achieve both 1 and 10 J/cm2 exposures, the same current, and therefore irradiance was used. Exposure time changed by a factor of 10 to achieve both doses, as can be seen in Table 2 below.

One PRP sample and one whole blood sample were exposed at high power (21 minutes, 51 seconds, at the voltages listed on the table 2), simultaneously, at wavelengths according to Table 1. This took approximately 2.5 hrs of exposure time, as the untreated controls were left in ambient conditions in the dark during any of the above 5 exposures for equal duration. After each exposure, the whole blood samples were recombined into a single centrifuge tube and the PRP isolation protocol performed as previously described. The resultant PRP was placed into a 6 well dish and returned to the incubator for 18-24 hours prior to ELISA performance.

TABLE 1

Wavelength Exposure Table

| Exposure # | PRP Sample | Whole Blood Sample |
|---|---|---|
| 1 | 420 nm | 660 nm |
| 2 | 660 nm | 420 nm |
| 3 | 530 nm | 597 nm |
| 4 | 597 nm | 850 nm |
| 5 | 850 nm | 530 nm |

TABLE 2

Experimental Conditions

| | | 1 J/cm$^2$ 7.6 mW/cm$^2$ 131 s (2 mm, 11 s) | | 10 J/cm$^2$ 7.6 mW/cm$^2$ 1311 s (21 min, 51 s) | |
|---|---|---|---|---|---|
| LED Bar | Wavelength (nm) | Current (A) | Current (mA) | Current (A) | Current (mA) |
| 72 | 420 | 0.160 | 160 | 0.160 | 160 |
| 32 | 530 | 0.450 | 450 | 0.450 | 450 |
| 100 | 660 | 0.278 | 278 | 0.278 | 278 |
| 400 | 597 | 0.550 | 550 | 0.550 | 550 |
| IR-850 | 850 | 0.097 | 97 | 0.097 | 97 |
| | | | Set @ 30 V | | Set @ 30 V |

One PRP sample and one whole blood sample were exposed at low power (2 min 11 sec at the previously described voltages), simultaneously, working from row 5 back to row 1 on the previously listed exposure Table 1. This took approximately 0.5 hrs of exposure time, as the untreated controls were left in ambient conditions in the dark during any of the above 5 exposures for equal duration.

After the exposures were completed, the whole blood samples were recombined into a single centrifuge tube and the PRP isolation protocol was performed using the 15 minutes @2100 rcf method. This again yielded clear distinction of layers.

The PRP generated from the whole blood exposure was placed into a 6 well dish and returned to the incubator for 18-24 hours prior to ELISA performance.

Finally, the positive controls were generated by applying 15.0 µL (this was adjusted to ensure it remained 10% of the total well volume) of a 2.28M CaCl$_2$) solution directly into each positive control designated well.

Approximately 21 hours (for the last exposed wells) after exposure, the PRP was collected into 1.5 mL centrifuge tubes for storage. The samples were placed in the laboratory refrigerator at 4 degrees until use in ELISAs. The CaCl$_2$) solution caused the positive control samples to form a thin gel layer across the top of the well. This layer was disrupted and all possible fluid was extracted from the gel remnants.

Example 2: Determination of Growth Factor Concentration in Light-Irradiated PRP and PRP Isolated from Light-Irradiated Whole Blood The PRP generated as described in sample 1 was tested for the concentration of PDGF and VEGF using ELISA (enzyme-linked immunosorbent assay).

In order to determine proper concentration for the final ELISAs, a dilution series was run on sample wells for both the PDGF-AA and VEGF-A using the untreated control plasma. An example (VEGF-A; the PDGF-AA was similar) of the protocol is described below for VEGF, the PDGF-AA protocol was similar, but used a different primary antibody.

VEGF-A ELISA Protocol

All reagents and samples were brought to room temperature (18-25° C.) before use. Assay Diluent B (Item E) was diluted 5-fold with deionized or distilled water before use. Assay Diluent A (Item D) was used for dilution of PRP samples. PRP samples were diluted as described below. The standard was prepared by briefly spinning a vial of Item C. 640 µL Assay Diluent A (for serum/plasma samples) was added into Item C vial to prepare a 50 ng/ml standard. The powder was dissolved thoroughly by a gentle mix. 60 µL of 50 ng/ml VEGF standard from the vial of Item C was added, into a tube with 440 µL Assay Diluent A to prepare a 6,000 pg/ml standard solution.

400 µL Assay Diluent A was pipetted into each tube. The stock standard solution was used to produce a dilution series with concentrations of 30,000 picograms (pg)/milliliter (mL), 10,000 pg/mL, 3,333 pg/mL, 1,111 pg/mL, 370.4 pg/mL, 123.5 pg/mL, 41.15 pg/mL, and 0 pg/mL. Standards were run in triplicate.

If the Wash Concentrate (20x) (Item B) contained visible crystals, it was warmed to room temperature and mixed gently until dissolved. 20 ml of Wash Buffer Concentrate was diluted into deionized or distilled water to yield 400 ml of 1x Wash Buffer.

The Detection Antibody vial (Item F) was briefly spun before use. 100 µL of 1x Assay Diluent B (Item E) was added into the vial to prepare a detection antibody concentrate and pipetted up and down to mix gently. The concentrate was stored at 4° C. for less than 5 days.

The detection antibody concentrate was diluted 100-fold with 1x Assay Diluent B (Item E) and used in the Assay Procedure. The HRP-Streptavidin concentrate vial (Item G) was briefly spun and pipetted up and down to mix gently before use. HRP-Streptavidin concentrate was diluted 300-fold with 1x Assay Diluent B (Item E). 40 µL of HRP-Streptavidin concentrate was added into a tube with 12 ml 1x Assay Diluent B to prepare a 300-fold diluted HRP-Streptavidin solution. This solution was mixed well and not stored.

100 µL of each standard and sample were added into appropriate wells. Wells were covered and incubated for 2.5 hours at room temperature with gentle shaking. The solution was discarded and wells were washed 4 times with 1x Wash Solution by filling each well with Wash Buffer (300 µL) using a multi-channel Pipette or autowasher. After the last wash, the remaining Wash Buffer was removed by aspirating or decanting, and the plate was inverted and blotted against clean paper towels.

100 µL of 1x prepared biotinylated antibody was added to each well. Samples and standards were incubated for 1 hour at room temperature with gentle shaking. The solution was then discarded, and the wash step repeated as described previously. 100 µL of prepared Streptavidin solution was added to each well. Samples and standards were incubated for 45 minutes at room temperature with gentle shaking. 6 8. The solution was then discarded, and the wash step repeated as described previously. 100 µL of TMB One-Step Substrate Reagent (Item H) was added to each well. Samples and standards were incubated for 30 minutes at room temperature in the dark with gentle shaking. 50 µL of Stop Solution (Item I) was added to each well, and the plates were read at 450 nm immediately.

The test results determined that all the samples were within range, although the VEGF-A ELISA demonstrated low levels and the PDGF-AA ELISA demonstrated that it would be safest to dilute the sample 1:10 to ensure that any stimulation of PDGF-AA would remain within range. VEGF-A ELISA samples were used undiluted.

All samples on the final ELISA were run in triplicate, including the negative/untreated controls and CaCl2 positive controls. The VEGF-A ELISA used was RayBiotech ELH-VEGF-A, Lot #: 1016170196 Expiration Oct. 16, 2018 and the PDGF-AA ELISA used was RayBiotech ELH-PDGFAA, Lot #: 1019170248 Expiration Oct. 19, 2018.

All optical densities (OD) were read using the μQuant Universal Microplate Spectrophotometer and related software. The data was generated and put into Microsoft Excel and then analyzed using the www.elisaanalysis.com/app website.

In Tables 3 and 4, WB=samples light-irradiated as whole blood before purification of PRP, PRP=samples light-irradiated as PRP, low dose=1 J/cm$^2$ and high dose=10 J/cm$^2$. (−) negative controls were treated in parallel to experimental samples, as described herein but not exposed to light. (+) controls were treated with CaCl$_2$ as described herein.

TABLE 3

PDGF-AA Statistical Significance Relative to Appropriate Untreated Control.

| Sample | P-Value from (Unpaired t-Test) | PDGF-AA % Change from Untreated Control |
|---|---|---|
| PRP High Dose 420 nm | 0.3 | −9.50% |
| PRP High Dose 530 nm | 0.02 | 13.50% |
| PRP High Dose 597 nm | 0.12 | 4.80% |
| PRP High Dose 660 nm | 0.04 | −24.60% |
| PRP High Dose 850 nm | 0.03 | −33.50% |
| PRP Low Dose 420 nm | 0.02 | 17.10% |
| PRP Low Dose 530 nm | 0.006 | 23.90% |
| PRP Low Dose 597 nm | 0.006 | −35.70% |
| PRP Low Dose 660 nm | 0.04 | 21.60% |
| PRP Low Dose 850 nm | 0.03 | 56.20% |
| WB High Dose 420 nm | 0.31 | 17.40% |
| WB High Dose 530 nm | 0.23 | −9.30% |
| WB High Dose 597 nm | 0.5 | 86.30% |
| WB High Dose 660 nm | 0.02 | 247.40% |
| WB High Dose 850 nm | 0.03 | 277.00% |
| WB Low Dose 420 nm | 0.13 | −18.30% |
| WB Low Dose 530 nm | 0.12 | 24.00% |
| WB Low Dose 597 nm | 0.11 | 25.40% |
| WB Low Dose 660 nm | 1 | 1.60% |
| WB Low Dose 850 nm | 0.67 | 5.40% |
| +Control PRP | 0.005 | 142.10% |
| +Control Whole Blood | 0.04 | 41.40% |

PDGF-AA ELISA results from Table 3 are plotted in FIG. 5, FIG. 6, FIG. 7, FIG. 9, and FIG. 10. In all cases, the percent change relative to an untreated control (i.e., a control not exposed to light) is shown on the Y-axis.

FIG. 5 compares percent change in PDGF in PRP isolated from whole blood irradiated with 850 nm light at 10 J/cm$^2$, versus PRP irradiated with the same wavelength and fluence of light. As can be seen from FIG. 5, irradiation of whole blood leads to a superior increase in the amount of PDGF in the PRP, while irradiation of PRP directly does not.

FIG. 6 compares PDGF levels in PRP isolated from whole blood treated with the two doses of 850 nm light, 1 J/cm$^2$ and 10 J/cm$^2$. As can be seen from FIG. 6, the amount of PDGF in the PRP increases with light dose.

FIG. 8 shows that light dependent increases in PDGF in PRP isolated from irradiated whole blood are dependent on the wavelength of light. Irradiation of whole blood with longer wavelengths of light, such as 660 nm and 850 nm, lead to increases in PDGF in the PRP, while irradiation of whole blood with shorter wavelengths of light did not lead to these increases in PDGF level.

TABLE 4

Statistical significance relative to appropriate untreated control for VEGF-A ELISA results.

| Sample | P-Value from (Unpaired t-Test) | VEGF-A % Change from Untreated Control |
|---|---|---|
| PRP High Dose 420 nm | 0.02 | 52.70% |
| PRP High Dose 530 nm | 0.06 | 20.40% |
| PRP High Dose 597 nm | 0.27 | 14.50% |
| PRP High Dose 660 nm | 0.46 | −5.00% |
| PRP High Dose 850 nm | 0.01 | −21.50% |
| PRP Low Dose 420 nm | 0.06 | 17.40% |
| PRP Low Dose 530 nm | 0.06 | 17.40% |
| PRP Low Dose 597 nm | 0.18 | 0.07% |
| PRP Low Dose 660 nm | 0.18 | 14.50% |
| PRP Low Dose 850 nm | 0.06 | 20.40% |
| WB High Dose 420 nm | 0.09 | 14.30% |
| WB High Dose 530 nm | 0.04 | −26.60% |
| WB High Dose 597 nm | 0.05 | −19.50% |
| WB High Dose 660 nm | 0.07 | 10.70% |
| WB High Dose 850 nm | 0.07 | 10.70% |
| WB Low Dose 420 nm | 0.42 | −5.30% |
| WB Low Dose 530 nm | 0.48 | 5.30% |
| WB Low Dose 597 nm | 0.62 | 5.30% |
| WB Low Dose 660 nm | 0.23 | −5.30% |
| WB Low Dose 850 nm | 0.1 | −23.10% |
| +Control PRP | 0.004 | 46.70% |
| +Control Whole Blood | 0.006 | 28.80% |

VEGF-A ELISA results from Table 4 are plotted in FIG. 7, FIG. 11, and FIG. 12. In all cases, the percent change relative to an untreated control (i.e., a control not exposed to light) is shown on the Y-axis. Except for a single outlying result at 660 nm and 10 J/cm$^2$ fluence, which was present in only 1 of 3 replicates, levels of VEGF in PRP from light irradiated whole blood or light irradiated PRP did not show the same increases as PDGF. While levels of VEGF increased slightly in light irradiated PRP these levels did not surpass increases in VEGF seen with a CaCl$_2$) control.

The ELISAs generated well grouped data and good standard curves for both VEGF-A and PDGF-AA. In reviewing the values, the LED treatment resulted in changes in protein levels in the plasma following exposures. These changes were variable between the high and low dose as well as the wavelengths. The positive Calcium Chloride controls demonstrated stimulation of both of the proteins tested.

The PDGF-AA ELISA positive controls demonstrated a 142.1% increase in the exposed plasma and only a 41.4% increase in the exposed whole blood. In contrast, the high dose LED exposed whole blood generated much larger positive changes in PDGF-AA relative to high dose LED exposed PRP. Conversely, the low dose LED exposure of whole blood generated lower positive changes relative to low dose exposed plasma. The largest changes seen were seen in whole blood exposed to high dose 850 nm (277.0%), 660 nm (274.4%) and 597 nm (86.3%) LEDs. The largest changes in directly exposed PRP were low dose 850 nm (56.2%) and 530 nm (23.9%).

The VEGF-A ELISA positive controls generated a 46.7% change in exposed PRP and 28.8% change in exposed whole blood. Overall, the total amounts of VEGF-A generated were small picogram amounts with the exception of the standards. In this instance, high LED dose seemed to generate larger positive changes than low LED dose in all instances.

The t-test generated statistical significance for VEGF-A and PDGF-AA levels for certain LEDs. This will allow for a lower volume of blood draw and eliminate the parameters that did not generate any statistical change. In general, VEGF-A levels were not very high. Selected wavelengths and exposure durations can now be modified to variable pulsing modes.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A method of making a light-irradiated plasma product from blood, the method comprising:
    (a) processing a quantity of whole blood by controlling a spectral content of light applied to the quantity of whole blood such that a concentration of a growth factor in the quantity of whole blood is increased, wherein controlling the spectral content of the applied light comprises providing light in a wavelength range of from 660 nm to 1500 nm; and
    (b) extracting a plasma product including the growth factor from the processed quantity of whole blood.

2. The method of claim 1, wherein controlling the spectral content of the applied light comprises providing light in a wavelength range from 600 nm to 900 nm and wherein the growth factor comprises a platelet-derived growth factor (PDGF).

3. The method of claim 1, further comprising controlling a radiant energy of the applied light.

4. The method of claim 3, wherein controlling the radiant energy of the applied light comprises controlling an exposure time of the applied light.

5. The method of claim 1, wherein controlling the spectral content of the applied light comprises irradiating the quantity of whole blood with a solid-state light source.

6. The method of claim 5, wherein the solid-state light source comprises a LED light source.

7. The method of claim 6, wherein the LED light source has a maximum spectral power in a wavelength range from 600 nm to 1500 nm.

8. The method of claim 1, wherein controlling the spectral content of the applied light further comprises irradiating a transparent vessel containing the quantity of whole blood with a spectrally-selective light source while the transparent vessel is housed in an enclosure that blocks exposure of the vessel to ambient light.

9. The method of claim 8, wherein the spectrally-selective light source comprises an LED light source.

10. The method of claim 1, further comprising administering a therapeutically effective amount of a composition including the plasma product to tissue of a subject in need thereof to promote tissue regeneration.

11. The method of claim 10, wherein a concentration of the growth factor in the composition is at least 50% higher than a concentration of the growth factor in an un-irradiated sample of platelet-rich plasma isolated from a source of the quantity of whole blood.

12. The method of claim 10, wherein the tissue regeneration comprises increased hair growth.

13. The method of claim 10, wherein the tissue regeneration comprises reduction of skin wrinkles.

14. The method of claim 3, wherein controlling the radiant energy of the applied light includes a radiant energy of at least 1 J/cm$^2$.

15. The method of claim 3, wherein controlling the radiant energy of the applied light includes a radiant energy of at least 10 J/cm$^2$.

16. The method of claim 10, wherein the quantity of whole blood is derived from the subject.

* * * * *